(12) United States Patent
Zheng et al.

(10) Patent No.: US 8,906,867 B2
(45) Date of Patent: Dec. 9, 2014

(54) PRODUCTION METHOD OF SOLID PREPARATION AND THE SOLID PREPARATIONS PRODUCED BY THE METHOD

(75) Inventors: Siji Zheng, Shanghai (CN); Bo Tan, Shanghai (CN)

(73) Assignees: Shanghai Zhongxi Pharmaceutical Company, Shanghai (CN); Shanghai Zhongxi Sunve Pharmaceutical Co., Ltd., Shanghai (CN)

( * ) Notice: Subject to any disclaimer, the term of this patent is extended or adjusted under 35 U.S.C. 154(b) by 92 days.

(21) Appl. No.: 13/519,256

(22) PCT Filed: Dec. 28, 2010

(86) PCT No.: PCT/CN2010/080349
§ 371 (c)(1),
(2), (4) Date: Jun. 26, 2012

(87) PCT Pub. No.: WO2011/079768
PCT Pub. Date: Jul. 7, 2011

(65) Prior Publication Data
US 2012/0322753 A1 Dec. 20, 2012

(30) Foreign Application Priority Data
Dec. 29, 2009 (CN) .......................... 2009 1 0247360

(51) Int. Cl.
| | | |
|---|---|---|
| A61K 9/16 | (2006.01) | |
| A61K 9/20 | (2006.01) | |
| A61K 31/519 | (2006.01) | |
| A61K 31/454 | (2006.01) | |
| A61K 31/496 | (2006.01) | |
| A61K 31/4985 | (2006.01) | |
| A61K 9/00 | (2006.01) | |

(52) U.S. Cl.
CPC ............. *A61K 9/2013* (2013.01); *A61K 9/1617* (2013.01); *A61K 9/1623* (2013.01); *A61K 9/1635* (2013.01); *A61K 9/1652* (2013.01); *A61K 9/2018* (2013.01); *A61K 9/2027* (2013.01); *A61K 9/2054* (2013.01); *A61K 9/2059* (2013.01); *A61K 31/454* (2013.01); *A61K 31/496* (2013.01); *A61K 31/4985* (2013.01); *A61K 31/519* (2013.01); *A61K 9/0056* (2013.01)
USPC ............. 514/26; 514/179; 514/220; 514/221; 514/225.8; 514/252.16

(58) Field of Classification Search
CPC . A61K 9/1617; A61K 9/2013; A61K 9/1623; A61K 31/519; A61K 31/454; A61K 31/496
USPC ............ 514/26, 179, 220, 221, 225.8, 252.16
See application file for complete search history.

(56) References Cited

U.S. PATENT DOCUMENTS

| | | | | |
|---|---|---|---|---|
| 4,664,915 | A | * | 5/1987 | Simonian ...................... 424/606 |
| 7,659,286 | B2 | * | 2/2010 | Dantzman et al. ............ 514/314 |
| 2011/0009416 | A1 | * | 1/2011 | Hsia et al. ..................... 514/249 |

FOREIGN PATENT DOCUMENTS

| | | |
|---|---|---|
| CN | 1205629 A | 1/1999 |
| CN | 102106807 A | 6/2011 |
| WO | WO 97/22335 A1 | 6/1997 |
| WO | WO 03/086343 A2 | 10/2003 |
| WO | WO 2011/079608 A1 | 7/2011 |

OTHER PUBLICATIONS

Wang Xiaolei, "Study on the micronization and improvement of Telmisartan's solubility," Chinese Master's Theses Full-Text Database, No. 8, pp. 25-26, Aug. 15, 2009 (with partial translation).
Liu HaoYing et al., "Preparation of micronized ciprofloxacin by reactive precipitation," *Journal of Beijing University of Chemical Technology*, vol. 35, No. 3, pp. 19-22, 2008 (with translation).
Yang Fang et al., "Micronization of naproxen particles by precipitation," *Journal of Beijing University of Chemical Technology*, vol. 33, No. 3, pp. 15-18, 2006 (with translation).
Oct. 8, 2010 International Search Report issued in PCT/CN2010/074703 (with translation).
Oct. 8, 2010 Written Opinion of the International Searching Authority issued in PCT/CN2010/074703 (with translation).
Mar. 31, 2011 International Search Report issued in PCT/CN2010/080349 (with translation).
Mar. 31, 2011 Written Opinion of the International Searching Authority in PCT/CN2010/080349 (with translation).
Mar. 12, 2012 Office Action issued in Chinese Application No. 200910247360.0 (with translation).
Chinese Pharmacopoeia 2005 vol. 2 Appendix XC, pp. 92-94 (with translation).
Chinese Pharmacopoeia 2005 vol. 2 Appendix VD, pp. 35-37 (with translation).
Chinese Pharmacopoeia 2005 vol. 2 Appendix IV A, pp. 27-28 (with translation).
Chinese Pharmacopoeia 2005 vol. 2 Appendix XE, p. 96 (with translation).

* cited by examiner

*Primary Examiner* — Brandon Fetterolf
*Assistant Examiner* — Yih-Horng Shiao
(74) *Attorney, Agent, or Firm* — Oliff PLC

(57) ABSTRACT

The production method prepares a solid preparation by dissolving water-insoluble and/or water indissolvable alkaline active pharmaceutical ingredient in an acidifier-containing acid solution to obtain medicated acid liquid; homogeneously mixing alkalizer, adjuvants and the medicated acid liquid, and carrying out wet granulation. The alkalizer is a reagent to reduce the acidity of the mixture of the alkalizer and the medicated acid liquid relative to the acidity of the medicated acid liquid. The preparation method avoids the problems in mechanical pulverization, such as environmental pollution, great loss and serious security risks. This method is simply operated, has high safety coefficient and is convenient for industrialized production. Also disclosed is the solid preparation produced by the method. The solid preparation produced by the method has better dissolution performance than that produced by prior art, and has better or at least equivalent stability and content uniformity with prior art.

21 Claims, No Drawings

PRODUCTION METHOD OF SOLID PREPARATION AND THE SOLID PREPARATIONS PRODUCED BY THE METHOD

TECHNICAL FIELD

The present invention relates to the pharmaceutical preparation field, specifically to a production method of solid preparation and the preparation produced by the method.

BACKGROUND ART

In the pharmaceutical preparation field, the particle size of active pharmaceutical ingredients closely relates to the process and the quality of solid preparations. In a specific pharmaceutical preparation process, the suitable particle size of active pharmaceutical ingredients is usually selected according to the solubility and biofilm permeability of drugs. For example, a smaller particle size can be selected to promote the absorption of a drug with poor solubility and drug dissolution in the process of rate-limiting absorption. For another example, if the compressibility of a drug is poor, it can be improved by selecting an appropriate particle size and adding appropriate adjuvants. Therefore, the selective control of the particle size of active pharmaceutical ingredients is often involved in the process of the drug solid preparation. At present, the selective control of the particle size of active pharmaceutical ingredients is realized mostly by selecting different methods and process conditions of mechanical pulverization.

However, the process of mechanical pulverization has the problems of dust, environmental pollution, and great loss and so on. For some high active drugs, it exist high security risks that the operators may have adverse reactions in the process of mechanical pulverization. For example, a considerable number of hypnotics such as eszopiclone and alprazolam, have high activity, which can quickly take hypnotic effect with inhaling a low dose. When the operators pulverize such drugs, it is easy to cause operators the adverse reaction of rapid hypnosis, which will result in an accident. For another example, when pulverizing some high-activity hormones or anti-tumor drugs, the operators are easy to have serious adverse drug reactions if inhaling or touching the drug powder.

Also, so far by the widely used general method of mechanical pulverization (such as conventionally used universal pulverizer), the average particle size is generally about 100 micron. The dissolution characteristic of solid preparation produced by this method is still not ideal.

In the process of mechanical pulverization, to an active ingredient of a high-activity drug whose dosage is lower (such as ≤5 wt %) in the solid preparation, it also involves the problem of dispersal uniformity when mixing with adjuvants. Usually, the active pharmaceutical ingredients can disperse homogeneously in the solid preparation by carrying on the method of equivalent diluting and escalating the active pharmaceutical ingredients and adjuvants. But the operation of this method is complicated, and it also has the problems of dust, environmental pollution, great loss, security risks in labor protection and so on.

In addition, it should be also considered that whether the performances of the product can meet the needs when a solid preparation is produced. For example, whether a better content uniformity can be guaranteed should be considered. For another example, stability is the focus when the quality of a solid preparation is inspected, which includes whether the chemical stability of active pharmaceutical ingredients, the content of the related substance (i.e. impurities), the state stability of solid preparations and dissolution stability etc. are within the limit of drug standards during the storage period of solid preparations.

Therefore, in view of the above defects of the existing technology, it is urgent to seek a preparation method which can not only avoid the above defects in the process of mechanical pulverization but also ensure various performances of solid preparations well.

CONTENTS OF INVENTION

The technical problem to be solved by the present invention is to overcome the defects in the existing production method of solid preparations that selective control of particle size of active pharmaceutical ingredients by mechanical pulverization will result in environmental pollution, serious security risks, great loss, and poor dissolution characteristics of the gained solid preparations and so on, and to aim at the water-insoluble or water indissolvable alkaline drugs, the present invention provides a production method and the solid preparations produced by the method, which is operated more simply, has less pollution and no above security risks and can guarantee the excellent dissolution performance, stability and content uniformity of the gained solid preparations and its gained solid preparations.

In order to solve the above technical problem, the inventor found a new path that uniquely dissolving water-insoluble and/or water indissolvable alkaline drugs by acid solution, and then reducing acidity in production process and restoring drugs to solid state, which can avoid many defects in the process of mechanical pulverization. And also, the inventor accidentally discovered that the solid preparations produced by this process have excellent dissolution performance, stability and content uniformity.

The production method of the invention includes the following steps: dissolving water-insoluble and/or water indissolvable alkaline active pharmaceutical ingredients in the acidifier-containing acid solution to obtain medicated acid liquid; then, homogeneously mixing alkalizer, adjuvants and the said medicated acid liquid, and carrying out wet granulation; wherein the said alkalizer is the reagent to reduce the acidity of the mixture of the alkalizer and the medicated acid liquid relative to the acidity of the medicated acid liquid.

In the present invention, the said water-insoluble and/or water indissolvable alkaline active pharmaceutical ingredients are selected from the existing active pharmaceutical ingredients with the above corresponding properties, which includes amphiprotic active pharmaceutical ingredients with both acidic and alkaline groups simultaneously. In the present field, the said alkaline active pharmaceutical ingredients are mostly weak alkaline active pharmaceutical ingredients. The present invention prefers the water-insoluble or water indissolvable alkaline drugs with higher activity and lower content in solid preparations (the content is generally lower than 20%, preferably lower than 5%, more preferably lower than 1%, the percentage is mass percentage). More specifically, the present invention prefers but not limits to eszopiclone, diazepam, estazolam, alprazolam, zopiclone, aripiprazole, risperidone, mifepristone, perphenazine, digoxinum, agomelatine, iloperidone, paliperidone, olanzapine, haloperidol, dipyridamole, carbimazole, metoclopramide, minoxidil or reserpine. In the production process, the percentage of water-insoluble and/or water indissolvable alkaline active pharmaceutical ingredient in the dry materials during wet granulation can be determined according to the conventional content of water-insoluble and/or water indissolvable alkaline active pharmaceutical ingredients in solid preparations. According to the need, in addition to the water-insoluble and/or water indissolvable alkaline active pharmaceutical ingredients, other active pharmaceutical ingredients can also be added for the production of compound solid preparations, such as compound solid preparations of olanzapine and fluoxertine hydrochloride, or mifepristone and anorethindrane dipropionate.

In the present invention, the said acidifier refers to the acid reagents that can make the water-insoluble and/or water indissolvable alkaline active pharmaceutical ingredients completely dissolved in the acidifier-containing acid solution. According to the common knowledge in the present field, the said acidifier should be pharmaceutically acceptable and compatible with the water-insoluble and/or water indissolvable alkaline active pharmaceutical ingredients. In the present invention, the said compatibility means coexistence without adverse effects. The said acidifier can be a single acidifying agent as well as a compound acidifying agent consisting of more than two components, which can be selected from a variety of acids, such as one or more among inorganic strong acid, inorganic mediate strong acid and organic weak acid, preferably selected from one or more among hydrochloric acid, citric acid, tartaric acid, malic acid, fumaric acid, succinic acid, maleic acid, lactic acid, acetic acid, hydrobromic acid, sulfuric acid, nitric acid and phosphoric acid, and more preferably from hydrochloric acid, citric acid, tartaric acid, malic acid, lactic acid, acetic acid or phosphoric acid. More specifically, the present invention particularly prefers the acidifiers below:

when the water-insoluble and/or water indissolvable alkaline active pharmaceutical ingredient is eszopiclone, the said acidifier is hydrochloric acid, citric acid, malic acid or tartaric acid, the best is hydrochloric acid;

when the water-insoluble and/or water indissolvable alkaline active pharmaceutical ingredient is zopiclone, the said acidifier is citric acid, hydrochloric acid, malic acid or tartaric acid, the best is citric acid;

when the water-insoluble and/or water indissolvable alkaline active pharmaceutical ingredient is aripiprazole, the said acidifier is selected from hydrochloric acid, citric acid, malic acid or lactic acid, the best is hydrochloric acid or citric acid;

when the water-insoluble and/or water indissolvable alkaline active pharmaceutical ingredient is risperidone, the said acidifier is hydrochloric acid, citric acid or tartaric acid, the best is hydrochloric acid or citric acid;

when the water-insoluble and/or water indissolvable alkaline active pharmaceutical ingredient is dipyridamole, the said acidifier is hydrochloric acid or citric acid;

when the water-insoluble and/or water indissolvable alkaline active pharmaceutical ingredient is iloperidone, the said acidifier is acetic acid or citric acid.

The dosage of the said acidifier is at least the minimum dosage which can completely dissolve the water-insoluble and/or water indissolvable alkaline active pharmaceutical ingredient, preferably 1~1.5 times over the minimum dosage, most preferably 1~1.05 times over the minimum dosage. The dosage of the acidifier which can make the water-insoluble and/or water indissolvable alkaline active pharmaceutical ingredient dissolved relates to many factors, such as acidifier type, solvent type, number of the hydrogen ions in acidifier which can combine with the alkaline centers of water-insoluble and/or water indissolvable alkaline active pharmaceutical ingredient, and preparation conditions of medicated acid liquid (e.g. temperature) and so on. Wherein, the said alkaline centers refer to groups or parts of water-insoluble and/or water indissolvable alkaline active pharmaceutical ingredient which can combine with hydrogen ions of acidifier molecules. Therefore, the said minimum dosage refers to the minimal dose of a certain acidifier which can just make the certain water-insoluble and/or water indissolvable alkaline active pharmaceutical ingredient dissolved under the preparation conditions of the same solvent and medicated acid liquid, and the said minimum dosage can be obtained by simple conventional method: under the preparation conditions of the same solvent and medicated acid liquid, the minimum dosage is obtained when a certain water-insoluble and/or water indissolvable alkaline active pharmaceutical ingredient is just dissolved by gradually increasing a certain acidifier's dosage. To be specific, the inventor has obtained by many experiments that the molar ratio of the acidifier to the water-insoluble and/or water indissolvable alkaline active pharmaceutical ingredient is generally 0.1~2.5, mostly 0.5~1.5. The present invention specially prefers the following dosages of acidifiers:

for eszopiclone, specially preferably hydrochloric acid with 0.75~1.05 times the molar dosage of it, or citrate acid with 0.9~1.1 times the molar dosage of it;

for zopiclone, specially preferably citrate acid with 0.9~1.1 times the molar dosage of it, or hydrochloric acid with 0.95~1.2 times the molar dosage of it;

for aripiprazole, specially preferably hydrochloric acid with 0.9~4.2 times the molar dosage of it, or citric acid with 0.8~1.3 times the molar dosage of it, or malic acid with 0.8~1.1 times the molar dosage of it;

for dipyridamole, specially preferably hydrochloric acid with 0.7~1.2 times the molar dosage of it, or citric acid with 0.7~1.1 times the molar dosage of it;

for risperidone, specially preferably hydrochloric acid with 0.8~2.1 times the molar dosage of it, or citric acid with 0.3~1.1 times the molar dosage of it, or tartaric acid with 0.25~1.1 times the molar dosage of it;

for iloperidone, specially preferably acetic acid with 1.4~2.7 times the molar dosage of it.

In the invention, the solvent of the said acidifier-containing acid solution may be water, organic solvent, or the mixture of water and organic solvent. According to the common knowledge of the present field, the selected solvent should be the one in which the ions of acidifier can be dissociated. For example, when the acidifier is inorganic, water or the mixture of water and organic solvent can be selected; when the acidifier is organic, water, the mixture of water and organic solvent, or organic solvent can be selected. If the solubility of the active pharmaceutical ingredient in some organic solvents is better than that in water, the mixture of water and the organic solvent is preferably selected to in favor of the dissolution of the active pharmaceutical ingredient and to reduce the dosage of the acid solution so as to facilitate subsequent granulation steps. The said organic solvent is selected from the acceptable solvents in the pharmaceutical field according to the principle that the solubility of the water-insoluble and/or water indissolvable alkaline active pharmaceutical ingredient in this organic solvent is better than that in water, and the water-miscible organic solvent is preferred, such as conventionally used water-soluble alcohols in the pharmaceutical field, like ethanol, propylene glycol, glycerin, acetone, isopropyl alcohol and tertiary butyl alcohol etc., preferably one or more selected from ethanol, acetone, propylene glycol and glycerol, particularly preferably ethanol. The concentration of the organic solvent can be selected optionally in the mixture of water and the organic solvent. The solvent dosage in the acid solution can make the drugs soluble at least, and is at least the minimum dosage of the granulating liquid needed for wet granulation. Generally the solvent dosage is 5~100% mass percentage of dry materials in wet granulation, and preferably 10~50%.

During the process for medicated acid liquid, some adjuvants can be added, such as adhesives, surfactants, solubilizers and the water-soluble carriers of solid dispersion and so on. It is preferable to add one or more among adhesives, surfactants, solubilizers and water-soluble carriers of solid dispersion, when or after the water-insoluble and/or water indissolvable alkaline active pharmaceutical ingredient is dissolved in the acidifier-containing acid solution, and then subsequent steps are carried out with the gained medicated acid liquid, which is to mix the medicated acid liquid homogeneously with the alkalizer and adjuvants to carry out wet granulation. Wherein, the dosage of water-soluble carriers of solid dispersion should be controlled less than that which can ensure the water-insoluble and/or water indissolvable alkaline active pharmaceutical ingredient completely dissolves in the acidifier-containing acid liquid, when the water-soluble carriers of solid dispersion and the water-insoluble and/or water indissolvable alkaline active pharmaceutical ingredient are added into the acidifier-containing acid liquid at the same time. And then, the water-soluble carriers of solid dispersion can also be added into again. The gained medicated acid liquid would be turbid liquid or viscous liquid with a large addition. The present invention particularly prefers one or more among povidone, polyethylene glycol (preferably polyethylene glycol 400-8000), sodium dodecyl sulfate, poloxamer, polyoxyethylenated castor oil, Tween 80, polyoxyl (40) stearate, lactose, mannitol, sucrose, hydroxypropyl-β-cyclodextrin, β-cyclodextrin and maltose. The dosage of the said surfactants and/or solubilizers prefers 0.05~5 times the mass of the water-insoluble and/or water indissolvable alkaline active pharmaceutical ingredient. The dosage of the said water-soluble carriers of solid dispersion prefers 1~10 times the mass of the water-insoluble and/or water indissolvable alkaline active pharmaceutical ingredient. According to the above procedure to add surfactants and/or solubilizers, it can increase the solubility of the water-insoluble and/or water indissolvable alkaline active pharmaceutical ingredient in the acid solution and reduce the solvent dosage so as to benefit the subsequent granulation steps. It is especially worth mentioning that, it can make the dissolution performance of solid preparations better, when adding one or more among surfactants, solubilizers and water-soluble carriers of solid dispersion according to the above procedure, especially water-soluble carriers of solid dispersion.

Preferably, in the preparation of the medicated acid liquid, it can appropriately increase the preparation temperature of medicated acid liquid through the conventional heating method such as hot water-bath, so as to benefit the dissolution of the active pharmaceutical ingredient. When the solvent is water, the preparation temperature preferably increases to 40~80° C. When the solvent is the mixture of water and organic solvent, it preferably increases to 40~70° C. When the solvent is ethanol, it preferably increases to 30~50° C.

In the present invention, the said adjuvants can be selected from any known and widely used adjuvants in this field, such as fillers, binders, disintegrants, adsorbent, lubricants and so on. The dosage of the said adjuvants can be selected according to the conventional knowledge in this field. Wherein, the said filler is preferred one or more among lactose, microcrystalline cellulose, starch, pregelatinized starch, mannitol, sucrose and maltitol. The said adhesive is preferred one or more among hypromellose, povidone, methyl cellulose and hydroxypropyl cellulose. The said disintegrant is preferred one or more among carboxymethyl starch sodium, low-substituted hydroxypropyl cellulose, crosslinked polyvinylpyrrolidone and croscarmellose sodium. The said lubricant is preferred colloidal silica (aerosil), sodium octadecyl fumarate, talcum powder or magnesium stearate. The dosage of the said adjuvants can be selected according to the conventional knowledge in the present field.

In the present invention, the said alkalizer refers to the reagents which can reduce the acidity of the mixture of the alkalizer and the medicated acid liquid relative to the acidity of the medicated acid liquid, for example, inorganic strong alkali (such as sodium hydroxide), strong alkali and weak acid salt (such as sodium carbonate, disodium hydrogen phosphate), as well as the conjugate base of organic weak acid (e.g., sodium citrate, sodium tartrate, sodium malate and sodium acetate), or the acid which acidity of is lower than strong acidic acidifier and can form buffer pair with the strong acidic acidifier (such as glycine and alanine). According to the conventional knowledge in this field, the said alkalizer should be pharmaceutically acceptable and compatible with the water-insoluble and/or water indissolvable alkaline active pharmaceutical ingredient.

The invention prefers the following types of groups of acidifier and alkalizer:

Type 1: the said acidifier is inorganic strong acid, and the said alkalizer is inorganic strong alkali, such as hydrochloric acid and sodium hydroxide.

Type 2: the said acidifier is inorganic strong acid, and the said alkalizer is the salt of inorganic weak acid and strong alkali, such as hydrochloric acid and sodium carbonate, hydrochloric acid and disodium hydrogen phosphate.

Type 3: the said acidifier is inorganic strong acid, and the said alkalizer is the salt of organic weak acid and strong alkali, such as hydrochloric acid and sodium citrate, hydrochloric acid and sodium tartrate, hydrochloric acid and sodium acetate, or hydrochloric acid and sodium malate.

Type 4: the said acidifier is organic weak acid, and the said alkalizer is the conjugate alkali of the organic weak acid, the acidifier and the alkalizer compose a conjugate acid-alkali buffer pair, such as the buffer pair which is composed of one or more among citric acid, tartaric acid, malic acid, fumaric acid, succinic acid, maleic acid, lactic acid and acetic acid and their corresponding conjugate alkali, preferably selected from one or more among the following buffer pairs: citric acid and sodium citrate, tartaric acid and sodium tartrate, malic acid and sodium malate, as well as acetic acid and sodium acetate.

Type 5: the said acidifier is organic weak acid, and the said alkalizer is inorganic strong alkali or the salt of inorganic weak acid and strong alkali, and the acidifier and the alkalizer compose a buffer pair, such as citric acid and sodium hydroxide, acetic acid and sodium hydroxide, citric acid and sodium carbonate, malic acid and sodium carbonate, malic acid and disodium hydrogen phosphate, or citric acid and disodium hydrogen phosphate.

Type 6: the said acidifier is inorganic strong acid, and the said alkalizer is weak acid which can compose a buffer pair with the inorganic strong acid, for example, hydrochloric acid and glycine, or hydrochloric acid and alanine.

Type 7: the said acidifier is inorganic mediate strong acid, and the said alkalizer is inorganic strong alkali, the salt of inorganic weak acid and strong alkali or the salt of organic weak acid and strong alkali, such as phosphoric acid and sodium hydroxide, phosphoric acid and sodium carbonate or phosphoric acid and disodium hydrogen phosphate.

The dosage of the said alkalizer is at least the one that can reduce the acidity of the mixture of the alkalizer and the medicated acid liquid relative to that of the medicated acid liquid. Preferably, the dosage of the acidifier and alkalizer meets the following relations: the value of formula 1 is 0.01~1.5, more preferably 0.3~1.2.

$$(\text{mole of alkalizer}*A)/(\text{mole of acidifier}*B) \quad \text{formula 1}$$

Wherein, when the acidifier and the alkalizier belong to type 1, 2 or 5, A equals to the total anionic valency of the alkalizer molecule minus the number of hydrogen ions in the alkalizer molecule;

when the acidifier and the alkalizier belong to type 1, 2, 3 or 6, B equals to the number of hydrogen ions in the acidifier molecule;

when the acidifier and the alkalizier belong to type 4, A/B equals 1;

when the acidifier and the alkalizier belong to type 5, B equals 1;

when the acidifier and the alkalizier belong to type 3 or 6, A equals 1;

The present invention particularly prefers:

for eszopiclone, hydrochloric acid and sodium carbonate whose dosages make the value of formula 1 equal 0.9~1.1, hydrochloric acid and sodium hydroxide whose dosages make the value of formula 1 equal 0.9~1.05, or citric acid and sodium citrate whose dosages make the value of formula 1 equal 0.4~1.2;

for zopiclone, citric acid and sodium citrate whose dosages make the value of formula 1 equal 0.6~1.2, hydrochloric acid and sodium carbonate whose dosages make the value of formula 1 equal 0.1~1, or hydrochloric acid and sodium hydroxide whose dosages make the value of formula 1 equal 0.1~1;

for aripiprazole, hydrochloric acid and sodium hydroxide whose dosages make the value of formula 1 equal 0.01~1.1, or citric acid and sodium citrate whose dosages make the value of formula 1 equal 0.1~1.3, or hydrochloric acid and sodium carbonate whose dosages make the value of formula 1 equal 0.2~1.0;

for risperidone, hydrochloric acid and sodium hydroxide whose dosages make the value of formula 1 equal 0.01~1.1, or citric acid and sodium citrate whose dosages make the value of formula 1 equal 0.1~1.5, or hydrochloric acid and glycine whose dosages make the value of formula 1 equal 0.1~1.3;

for dipyridamole, hydrochloric acid and sodium hydroxide;

for iloperidone, acetic acid and sodium hydroxide whose dosage make the value of formula 1 equal 0.99~1.01.

For some water-insoluble and/or water indissolvable alkaline active pharmaceutical ingredients, solid preparations can still have better stability, in the case of very little alkalizer dosage, but on the premise of no effect on the stability of the preparations, the reduction of acidity by appropriately increasing the alkalizer dosage can reduce the migration of pharmaceutical active ingredients in the process of preparation and is conducive to relieving pH value of solid preparations.

In this invention, the said wet granulation can be carried on by conventional steps and conditions belonging to the category of wet granulation in this field, such as extrusion granulation (such as extrusion by swing machine, screw extrusion and rotating extrusion etc.), stirring granulation, fluidized spray granulation, centrifugal spray granulation and so on. The wet granulation which has little limit on the dosage of granulation solution, such as fluidized spray granulation and centrifugal spray granulation, can be selected when the dosage of the water-insoluble and/or water indissolvable alkaline active pharmaceutical ingredient is larger in solid preparations (generally greater than 20%), or the solubility of it is lower in acidifier-containing acid liquid, which can be dissolved by only a large amount of acidic liquid Preferably, the specific mode of operation which refers to the said homogeneously mixing alkalizer, adjuvants and the said medicated acid liquid, and carrying out wet granulation is selected from anyone of the following methods: method (1) homogeneously mixing the alkalizer or the alkalizer-containing solution with the adjuvants, and then homogeneously mixing them with the medicated acid liquid, and carrying on extrusion granulation or stirring granulation; method (2) homogeneously mixing the medicated acid liquid with the alkalizer or the alkalizer-containing solution to obtain a granulating solution, and then carrying on extrusion granulation, stirring granulation, fluidized spray granulation or centrifugal spray granulation with the granulating solution and the adjuvants; method (3) homogeneously mixing the medicated acid liquid with the adjuvants, and then homogeneously mixing them with the alkalizer-containing solution, and carrying on extrusion granulation or stirring granulation; method (4) homogeneously mixing the medicated acid liquid, the adjuvants whose dosage is below one-third, and the alkalizer or the alkalizer-containing solution (the specific operation can be: first homogeneously mixing the adjuvants whose dosage is below one third, and the alkalizer or the alkalizer-containing solution, and then mixing the gained mixture with the medicated acid liquid; or, homogeneously mixing the adjuvants whose dosage is below one-third with the medicated acid liquid, and then homogeneous mixing them with the alkalizer or the alkalizer-containing solution), and then mixing them with the left adjuvants and carrying on extrusion granulation or stirring granulation. The said adjuvants whose dosage is below one-third are preferably water-soluble adjuvants. The said below one-third usually can be below one-fifth to one-tenth. The said alkalizer-containing solution refers to the solution gained by dissolving the alkalizer with a small dosage of solvent according to the conventional operations in this field, which facilitates the homogeneously mixing step; the said solvent can be water, organic solvent or the mixture of water and organic solvent. The said organic solvent is as mentioned above.

After the wet granulation is completed, solid granule preparations can be obtained directly, or pharmaceutical intermediates can be obtained which will be made into other forms of solid preparations such as tablets or capsules etc. through further conventional steps.

In the present invention, the mentioned optimal conditions can be optionally combined based on the general knowledge in this field to obtain preferred embodiments.

In the present invention, the used reagents and materials can be commercially available, and some materials can be prepared by methods in existing documents.

Further, the present invention also relates to the solid preparations produced by the mentioned method.

The positive effects of the present invention are that the preparation method in this invention avoids the defects of serious pollution during the mechanical pulverization, great loss and high security risks. This process is simply operated, has high safety coefficient and is convenient for industrialized production. The solid preparations in this invention have good dissolution characteristic, high bioavailability, little individual difference and also have better stability and content uniformity.

SPECIFIC MODE FOR CARRYING OUT THE INVENTION MODEL

Then the present invention is further illustrated by the following embodiments, but is not limited by the following embodiments.

In the following embodiments, the experimental methods without specific conditions, can be carried on by conventional conditions or the conditions recommended by manufacturers. Drug specification is count as the dosage of active pharmaceutical ingredient, for example 2 mg/tablet which refers to that one tablet contains 2 mg of active pharmaceutical ingredient. Dosage unit is gram, and percentage is mass percentage. Mass percentage of drug and solvent refers to the one in dry materials in wet granulation. Wherein, solvent dosage includes the water in water solution of acidifier and alkalizer.

COMPARISON EXAMPLES 1~2 AND EXAMPLES 1~2

Prescription and Preparation Method of Aripiprazole Granules

|  | Contrastive Example 1 | Contrastive Example 2 | Example 1 | Example 2 |
| --- | --- | --- | --- | --- |
| Drug | Aripiprazole 5 (2.4%, sieved by 100 mesh sieve) | Aripiprazole 5 (2.4%, micronization treatment, average diameter 25 μm) | Aripiprazole 5 (2.4%, without pretreatment) | Aripiprazole 5 (2.4%, without pretreatment) |
| Adjuvant | Lactose 200 | Lactose 200 | Lactose 200 | Lactose 185, Sucrose 15, Tween-80 0.38 |
| Solvent | 75% Aqueous ethanol solution 20 (9.8%) | 75% Aqueous ethanol solution 20 (9.8%) | 75% Aqueous ethanol solution 15.5 (9.7%) | 75% Aqueous ethanol solution 15.5 (9.7%) |
| Acidifier |  |  | 10% Aqueous hydrochloric acid solution 4.5 (mole ratio of it to aripiprazole is 1.11) | 10% Aqueous hydrochloric acid solution 4.5 (mole ratio of it to aripiprazole is 1.11) |
| Alkalizer |  |  | Sodium carbonate 0.7(the value of fomula 1 is 1.07) | Sodium carbonate 0.7( the value of fomula 1 is 1.07) |
| Preparation Technology | Grind aripiprazole by universal pulverizer and then make it pass through 100 mesh sieve; homogeneously mix it with lactose; add 75% aqueous ethanol solution, stir and made into soft material; carry out extrusion granulation; finish granule after drying wet granules. | Carry on micronization treatment on aripiprazole, homogeneously mix it with lactose; add 75% aqueous ethanol solution, stir and made into soft material; carry out extrusion granulation; finish granule after drying wet granules. | Dissolve aripiprazole and 10% aqueous hydrochloric acid solution in 75% aqueous ethanol solution; heat them with a water bath at about 50° C. to prepare medicated acid liquid; homogeneously mix lactose and sodium carbonate, and add the medicated acid liquid; stir and made into soft material; carry out extrusion granulation; finish granule after drying wet granules. | Dissolve aripiprazole and 10% aqueous hydrochloric acid soltuion in 75% aqueous ethanol solution; heat it with a water bath at about 50° C.; add sucrose and tween-80 and homogeneously mix them to prepare medicated acid liquid; homogeneously mix lactose and sodium carbonate and then add the medicated acid liquid, stir and made into soft material; carry out extrusion granulation; finish granule after drying wet granules. |

CONTRASTIVE EXAMPLES 3 AND EXAMPLES 3 AND 4

Prescription and Preparation Method of Aripiprazole Tablets (5 mg/tablet)

|  | Contrastive Example 3 | Example 3 | Example 4 |
| --- | --- | --- | --- |
| Drug | Aripiprazole 5 (4.4%, micronization treatment, average diameter 25 μm) | Aripiprazole 5 (4.2%, without pretreatment) | Aripiprazole 5 (4.4%, without pretreatment) |
| Adjuvant | Lactose 70, Microcrystalline Cellulose30, Carboxymethyl Starch Sodium 6, Povidone K30 2, Magnesium Stearate 0.9 | Lactose 70, Microcrystalline Cellulose 30, Carboxymethyl Starch Sodium 6, Povidone K30 2, Magnesium Stearate 0.9 | Lactose 40, Microcrystalline Cellulose 60, Carboxymethyl Starch Sodium 6, Povidone K30 2, Magnesium Stearate 0.9 |
| Solvent | 75% Aqueous ethanol solution 22 (19.3%) | 75% Aqueous ethanol solution 22 (18.7%) | 75% Aqueous ethanol solution 18 (23.0%) |
| Acidifier | \ | Citric Acid Monohydrate 2.5 (molar ratio of it to aripiprazole is 1.07) | 10% Aqueous HCl solution 4.2 (molar ratio of it to aripiprazol is 1.03) |
| Alkalizer | \ | Sodium Citrate Dihydrate 1.5 (the value of fomula 1 is 0.43) | 10% Aqueous NaOH solution 4.6 (the value of fomula 1 is 1.00) |
| Preparation Technology | Carry on micronization treatment on aripiprazole (average diameter 25 μm); make microcrystalline cellulose, carboxymethyl starch sodium and lactose pass through 80 mesh sieve; mix aripiprazole with the equivalent microcrystalline cellulose and dilute, and add the left microcrystalline cellulose gradually; homogeneously mix them with lactose and 70% amount of carboxymethyl starch sodium; carry out stirring granulation with the above mixture and povidone K30 which is dissolved in 75% aqueous ethanol solution, finish granule after | Dissolve aripiprazole, citric acid and povidone K30 in 75% aqueous ethanol solution, heat them with a water bath at about 60° C. to prepare medicated acid liquid; homogeneously mix lactose, microcrystalline cellulose, 70% amount of carboxymethyl starch sodium and sodium citrate; add the medicated acid liquid to carry out stirring granulation, finish granule after drying wet granules, add | Dissolve aripiprazole, povidone K30 and 10% aqueous HCl solution in 75% aqueous ethanol solution, heat them with a water bath at about 50° C., stir and dissolve, add 20% amount of lactose and stir to prepare medicated acid liquid; homogeneously mix the left lactose, microcrystalline cellulose and 70% amount of carboxymethyl starch sodium; add the medicated acid liquid and mix; add 10% aqueous NaOH solution while stirring, and made into soft material; carry out extrusion granulation, finish granule after |

-continued

| | Contrastive Example 3 | Example 3 | Example 4 |
|---|---|---|---|
| | drying, add magnesium stearate and the left carboxymethyl starch sodium, homogeneously mix and press. | magnesium stearate and the left 30% carboxymethyl starch sodium, homogeneously mix and press. | drying wet granules; add magnesium stearate and the left 30% carboxymethyl starch sodium, homogeneously mix and press. |

CONTRASTIVE EXAMPLES 4 AND 5

Prescription and Preparation Method of Aripiprazole Orally Disintegrating Tablets (5 mg/tablet)

| | Contrastive Example 4 | Example 5 |
|---|---|---|
| Drug | Aripiprazole 5 (2.5%, sieved by 100 mesh sieve) | Aripiprazole 5(2.5%, without pretreatment) |
| Adjuvant | Mannitol 120, Microcrystalline Cellulose 60, Crosslinked Polyvinylpyrrolidone 11, Aspartame 1, Magnesium Stearate 1.5 | Mannitol 120, Microcrystalline Cellulose 60, Crosslinked Polyvinylpyrrolidone 11, Aspartame 1, Magnesium Stearate 1.5 |
| Solvent | 75% Aqueous ethanol solution 24 (12.1%) | 75% Aqueous ethanol solution 16 (13.9%) |
| Acidifier | \ | 5% Aqueous HCl solution 8 (molar ratio of it to aripiprazole is 0.98) |
| Alkalizer | \ | 5% Aqueous NaOH solution 3.8(the value of fomula 1 is 0.43) |
| Preparation Technology | Dissolve aripiprazole (sieved by 100 mesh sieve, average diameter 89.51 μm) in 75% aqueous ethanol solution, stir and disperse; homogeneously stir and mix mannitol, microcrystalline cellulose and aspartame; add the above solution, stir and made into soft material, and carry out extrusion granulation; finish granule after drying wet granules; add magnesium stearate and crosslinked polyvinylpyrrolidone, homogeneously mix and press. | Dissolve aripiprazole and 5% aqueous HCl solution in 75% aqueous ethanol solution, heat them with a water bath at about 65° C., stir and dissolve to form medicated acid liquid; homogeneously stir and mix mannitol, microcrystalline cellulose, aspartame and 5% aqueous NaOH solution, and add the above solution, stir and made into soft material, carry out extrusion granulation, finish granule after drying wet granules; add magnesium stearate and crosslinked polyvinylpyrrolidone, homogeneously mix and press. |

CONTRASTIVE EXAMPLE 5 AND EXAMPLE 6

Prescription and Preparation Method of Eszopiclone Tablets (3 mg/tablet)

| | | Contrastive Example 5 | Example 6 |
|---|---|---|---|
| Tablet core | Drug | Eszopiclone 3(3.0%, sieved by 100 mesh sieve) | Eszopiclone 3(2.9%, without pretreatment) |
| | Adjuvant | Lactose 62.4, Carboxymethyl Starch Sodium 5, Hypromellose 0.33, Starch 30, Magnesium Stearate 0.6 | Lactose 62.4, Carboxymethyl Starch Sodium 5, Hypromellose 0.33, Starch 30, Magnesium Stearate 0.6 |
| | Solvent | Water 22 (21.7%) | Water 22 (20.9%) |
| | Acidifier | \ | Citric Acid Monohydrate1 1.8 (molar ratio of it to Eszopiclone is 1.11) |
| | Alkalizer | \ | Sodium Citrate Dihydrate 2 (the value of fomula 1 is 0.79) |
| | Preparation Technology | Grind eszopiclone by pulverizer and then make it pass through 100 mesh sieve; homogeneously mix it with starch, lactose and ⅔ amount of carboxymethyl starch sodium, disperse hypromellose with 80° C. hot water, and add water to dissolve; stir the above mixture and made into soft material, carry out extrusion granulation, finish granule after drying wet granules, add magnesium stearate and ⅓ amount of carboxymethyl starch sodium, homogeneously mix and press. | Make eszopiclone, citric acid and water into medicated acid liquid; homogeneously mix lactose, starch and ⅔ amount of carboxymethyl starch sodium and sodium citrate, add the medicated acid liquid, stir and made into soft material, carry out extrusion granulation, finish granule after drying wet granules, add magnesium stearate and ⅓ amount of carboxymethyl starch sodium, homogeneously mix and press. |
| Coating | Materials | Gastric soluble opadry 4, Water 18 | |
| | Preparation Technology | Stir when adding opadry powder in water, and continue to stir for 45 mins after adding to make coating solution, and carry out film-coating on the tablet core. | |

EXAMPLE 7

Prescription and Preparation Method of Eszopiclone Capsules (3 mg/tablet)

Make the granules before pressing in Example 6 pass through 30 mesh sieve and add them into hard capsules.

EXAMPLES 8 AND 9

Prescription and Preparation Method of Eszopiclone Tablets

|  |  | Example 8 (3 mg/tablet) | Example 9 (2 mg/tablet) |
|---|---|---|---|
| Tablet core | Alkaline Active Pharmaceutical Ingredient | Eszopiclone 3 (2.9%, without pretreatment) | Eszopiclone 2 (2.8%, without pretreatment) |
|  | Adjuvant | Lactose 62.4, Microcrystalline Cellulose 30, Hydroxypropylcellulose 5, Poloxamer 1, Hypromellose 0.33, Colloidal Silicon Dioxide 0.2, Magnesium Stearate 0.6 Water 22 (20.92) | Lactose 40, Microcrystalline Cellulose 25, Povidone K30 1.5, Mannitol 2, Carboxymethyl Starch Sodium 1, Colloidal Silicon Dioxide 0.2, Magnesium Stearate 0.3 Water 13 (22.9%) |
|  | Acidifier | Citric Acid Monohydrate 1.65 (molar ratio of it to Eszopiclone is 1.02) | 5% Aqueous HCl solution 3.8 (molar ratio of it to Eszopiclone is 1.01) |
|  | Alkalizer | Sodium Citrate Dihydrate 1 (the value of fomula 1 is 0.43) | $Na_2CO_3$ 0.27 (the value of fomula 1 is 0.98) |
|  | Preparation Technology | Disperse hypromellose by 80° C. hot water, add water and stir to dissolve, make it and eszopiclone, poloxamer, citric acid and the left water into medicated acid liquid, homogeneously mix lactose, microcrystalline cellulose, hydroxypropylcellulose and sodium citrate, add the medicated acid liquid and carry out extrusion granulation, finish granule after drying wet granules, add magnesium stearate and colloidal silicon dioxide, homogeneously mix and then press. | Make eszopiclone, mannitol, povidone K30, 5% aqueous HCl solution and water into medicated acid liquid; homogeneously mix lactose, microcrystalline cellulose and carboxymethyl starch sodium, add the medicated acid liquid and carry out mixing granulation, add $Na_2CO_3$ solution (dissolving $Na_2CO_3$ in a little water) and then continue stirring granulation, finish granule after drying wet granules, add magnesium stearate and colloidal silicon dioxide, homogeneously mix and then press. |
| Coating | Coating Materials | Gastric soluble opadry 4, Water 18 | Gastric soluble opadry 3, Water 13 |
|  | Preparation Technology | Stir when adding opadry powder in water, and continue to stir for 45 mins after adding to make coating solution, and carry out film-coating on the tablet core. |  |

EXAMPLES 10 AND 11

Prescription and Preparation Method of Eszopiclone Tablets

|  |  | Example 10 (1 mg/tablet) | Example 11 (2 mg/tablet) |
|---|---|---|---|
| Tablet Core | Drug | Eszopiclone 1 (1.5%, without pretreatment) | Eszopiclone 2 (2.8%, without pretreatment) |
|  | Adjuvant | Lactose 40, Starch 20, Carboxymethyl Starch Sodium 1, Sucrose 2, Magnesium Stearate 0.3, Colloidal Silicon Dioxide 0.1 Water 12 (24.7%) | Lactose 40, Microcrystalline Cellulose 25, Povidone K30 2, Magnesium Stearate 0.4, Colloidal Silicon Dioxide 0.2 Water 30 (42.4%) |
|  | Acidifier | 5% Aqueous HCl solution 2 (molar ratio of it to Eszopiclone is 1.07) | Citric Acid Monohydrate 0.98 (molar ratio of it to Eszopiclone is 0.91) |
|  | Alkalizer | 5% Aqueous NaOH solution 2.2 (the value of fomula 1 is 1) | Sodium Citrate Dihydrate 0.22 (the value of fomula 1 is 0.16) |
|  | Preparation Technology | Make eszopiclone, sucrose, 5% aqueous HCl solution and water into medicated acid liquid; homogeneously mix lactose, starch, carboxymethyl starch sodium and 5% aqueous NaOH solution, add the medicated acid liquid and carry out stirring granulation, finish granule after drying wet granules, add magnesium stearate and colloidal silicon dioxide, homogeneously mix and then press. | Make eszopiclone, povidone K30, citric acid and water into medicated acid liquid, stir when adding sodium citrate (dissolved in a little water) to obtain the granulation solution. Add lactose and microcrystalline cellulose in fluidized spray granulator, and carry on fluidized spray granulation, finish granule and then add magnesium stearate and colloidal silicon dioxide, homogeneously mix and then press. |
| Coating | Coating Materials | Premix of film-coating (Gastric soluble opadry) 2.5, Water 11 | Hypromellose 1.8, Polyethyleneglycol-6000 0.3, Titanium Dioxide 0.4, Water 15 |
|  | Preparation Technology | Stir when adding opadry power in water, and continue to stir for 45 mins after adding to make coating solution, and carry out film-coating on the tablet core. | Disperse hypromellose by 80° C. hot water, then add water and stir to dissolve, add polyethyleneglycol-6000 and homogenized titanium dioxide to form the coating solution, and carry out film-coating on the tablet core. |

CONTRASTIVE EXAMPLE 6 AND EXAMPLES 12 AND 13

Prescription and Preparation Method of Zopiclone Tablets

|  |  | Contrastive Example 6 (3.75 mg/tablet) | Example 12 (3.75 mg/tablet) | Example 13 (2.5 mg/tablet) |
|---|---|---|---|---|
| Tablet core | Drug | Zopiclone 3.75 (3.4%, sieved by 100 mesh sieve) | Zopiclone 3.75 (3.3%, without pretreatment) | Zopiclone 2.5 (2.9%, without pretreatment) |
|  | Adjuvant | Lactose 70, Carboxymethyl Starch Sodium 5, Starch 30, Hypromellose 0.4, Magnesium Stearate 0.6 | Lactose 70, Carboxymethyl Starch Sodium 5, Starch 30, Hypromellose 0.4, Magnesium Stearate 0.6 | Lactose 37.5, Microcrystalline Cellulose 37.5, Carboxymethyl Starch Sodium 4.2, Polyethyleneglycol-6000 1, Hypromellose 0.5, Magnesium Stearate 0.5, Colloidal Silicon Dioxide 0.15 |
|  | Solvent | Water 22 (20.1%) | Water 22 (19.2%) | Water 17 (19.5%) |
|  | Acidifier | \ | Citric Acid Monohydrate 2.2 (molar ratio of it to Zopiclone is 1.09) | Citric Acid Monohydrate 1.3 (molar ratio of it to Zopiclone is 0.96) |
|  | Alkalizer | \ | Sodium Citrate Dihydrate 2.5 (the value of fomula 1 is 0.81) | Sodium Citrate Dihydrate 2.2 (the value of fomula 1 is 1.21) |
|  | Preparation Technology | Grind zopiclone by pulverizer and then make it pass through 100 mesh sieve; homogeneously mix it with starch, lactose and ⅔ amount of carboxymethyl starch sodium; disperse hypromellose by 80° C. hot water, then add water and stir to dissolve, stir the above mixture and made into soft material, carry on extrusion granulation, finish granule after drying wet granules, add magnesium stearate and ⅓ amount of carboxymethyl starch sodium, homogeneously mix and then press. | Disperse hypromellose by 80° C. hot water, then add water and stir to dissolve, and add zopiclone, citric acid and water to form medicated acid liquid; homogeneously mix lactose, starch, ⅔ amount of carboxymethyl starch sodium and sodium citrate, add the medicated acid liquid, stir and made into soft material, finish granule after drying wet granules, add magnesium stearate and ⅓ amount of carboxymethyl starch sodium, homogeneously mix and then press. | Disperse hypromellose by 80° C. hot water, then add water and stir to dissolve, and add zopiclone, polyethyleneglycol-6000, citric acid and water to form medicated acid liquid, homogeneously mix lactose, microcrystalline cellulose, ⅔ amount of carboxymethyl starch sodium and sodium citrate, add the medicated acid liquid and carry out stirring granulation, finish granule after drying wet granules, add magnesium stearate, colloidal silicon dioxide and ⅓ amount of carboxymethyl starch sodium, homogeneously mix and then press. |
| Coating | Materials | Gastric soluble opadry 4.5, Water 19 |  | Gastric soluble opadry 3.5, Water 15 |
|  | Preparation Technology | Stir when adding opadry powder in water, and continue to stir for 45 mins after adding to make the coating solution, and carry out film-coating on the tablet core. |  |  |

EXAMPLES 14 AND 15

Prescription and Preparation Method of Zopiclone Tablets (2.5 mg/tablet)

|  |  | Example 14 | Example 15 |
|---|---|---|---|
| Tablet core | Drug | Zopiclone 2.5 (3.3%, without pretreatment) | Zopiclone 2.5 (4.2%, without pretreatment) |
|  | Adjuvant | Lactose 40, Microcrystalline Cellulose 25, Carboxymethyl Starch Sodium 1, Mannitol 2, Poloxamer 1, Magnesium Stearate 0.3, Colloidal Silicon Dioxide 0.2 | Lactose 30, Carboxymethyl Starch Sodium 3, Microcrystalline Cellulose 20, Polyethyleneglycol-6000 1, Crospovidone 2, Colloidal Silicon Dioxide 0.15, Magnesium Stearate 0.3 |
|  | Solvent | Water 8, 95% aqueous ethanol solution 4 (16.0%) | Water 11 (25.8%) |
|  | Acidifier | Citric Acid Monohydrate 1.6 (molar ratio of it to Zopiclone is 1.19) | 5% Aqueous HCl solution 4.5 (molar ratio of it to Zopiclone is 0.96) |
|  | Alkalizer | Sodium Citrate Dihydrate 1.4 (the value of fomula 1 is 0.63) | $Na_2CO_3$ 0.07 (the value of fomula 1 is 0.21) |
|  | Preparation Technology | Make zopiclone, poloxamer, mannitol, citric acid, 95% aqueous ethanol solution and water into medicated acid liquid, homogeneously mix lactose, microcrystalline cellulose, carboxymethyl starch sodium and sodium citrate, add the medicated acid liquid and stir to made into soft material, carry out extrusion granulation, finish granule after drying wet granules, add magnesium stearate and colloidal silicon dioxide, homogeneously mix and then press. | Make zopiclone, polyethyleneglycol-6000, 5% aqueous HCl solution and ⅔ amount of water into medicated acid liquid, homogeneously mix lactose, microcrystalline cellulose, ⅔ amount of carboxymethyl starch sodium and crospovidone, add $Na_2CO_3$ solution (prepared with ⅓ amount of water) and mix, add the medicated acid liquid and carry out stirring granulation, finish granule after drying wet granules, add magnesium stearate, ⅓ amount of carboxymethyl starch sodium and colloidal silicon dioxide, homogeneously mix and then press. |
| Coating | Materials | Premix of film-coating (Gastric soluble opadry) 3, Water 13 | Premix of film-coating (Gastric soluble opadry) 2.1, Water 9 |
|  | Preparation Technology | Stir when adding opadry powder in water, and continue to stir for 45 mins after adding to make the coating solution, and carry out film-coating on the tablet core. | Stir when adding opadry powder in water, and continue to stir for 45 mins after adding to make the coating solution, and carry out film-coating on the tablet core. |

EXAMPLES 16 AND 17

Prescription and Preparation Method of Zopiclone Tablets (2.5 mg/tablet)

|  |  | Example 16 | Example 17 |
|---|---|---|---|
| Tablet Core | Drug | Zopiclone 2.5 (1.90%, without pretreatment) | Zopiclone 2.5 (2.8%, without pretreatment) |
|  | Adjuvant | Lactose 60, Microcrystalline Cellulose 60, Croscarmellose Sodium 5, Magnesium Stearate 0.8, Talcum Powder 3 | Lactose 37.5, Microcrystalline Cellulose 37.5, Carboxymethyl Starch Sodium 4.2, Polyethyleneglycol-6000 1, Hypromellose 0.5, Magnesium Stearate 0.5, Colloidal Silicon Dioxide 0.15 |
|  | Solvent | Water 2, 95% Aqueous ethanol solution 12 (17.8%) | Water 17 (19.3%) |
|  | Acidifier | 5% Aqueous HCl solution 5 (molar ratio of it to Zopiclone is 1.06) | Citric Acid Monohydrate 2(molar ratio of it to Zopiclone is 1.48) |
|  | Alkalizer | 5% Aqueous NaOH solution 5(the value of fomula 1 is 0.91) | Sodium Citrate Dihydrate 2.2 (the value of fomula 1 is 0.79) |
|  | Preparation Technology | Make zopiclone, 5% aqueous HCl solution, 95% aqueous ethanol solution and water into medicated acid liquid, homogeneously mix lactose, microcrystalline cellulose and ⅔ amount of croscarmellose sodium, add 5% aqueous NaOH solution and homogeneously mix, add the medicated acid liquid and carry out stirring granulation, finish granule after drying wet granules, add magnesium stearate, ⅓ amount of croscarmellose sodium and talcum powder, homogeneously mix and then press. | Disperse hypromellose by 80° C. hot water, then add water and stir to dissolve, mix it with zopiclone, polyethyleneglycol-6000, citric acid and water to form solution, add 65% amount of lactose to form medicated acid liquid, homogeneously mix the left lactose, microcrystalline cellulose, ⅔ amount of carboxymethyl starch sodium and sodium citrate, add the medicated acid liquid and carry out stirring granulation, finish granule after drying wet granules, add magnesium stearate, colloidal silicon dioxide and ⅓ amount of carboxymethyl starch sodium, homogeneously mix and then press. |
| Coating | Materials | Premix of film-coating (Gastric soluble opadry) 5, Water 21 | Premix of film-coating (Gastric soluble opadry) 3.5, Water 15 |
|  | Preparation Technology | Stir when adding opadry powder in water, and continue to stir for 45 mins after adding to make the coating solution, and carry out film-coating on the tablet core. | Stir when adding opadry powder in water, and continue to stir for 45 mins after adding to make the coating solution, and carry out film-coating on the tablet core. |

CONTRASTIVE EXAMPLE 7 AND EXAMPLE 18

Prescription and Preparation Method of Risperidone Tablets (1 mg/tablet)

|  |  | Contrastive Example 7 | Example 18 |
|---|---|---|---|
| Tablet core | Drug | Risperidone 1 (1.0%, pulverization, average diameter 62 μm) | Risperidone 1(1.0%, without pretreatment) |
|  | Adjuvant | Mannitol 50, Microcrystalline Cellulose 50, Croscarmellose Sodium 2, Magnesium Stearate 0.9 | Mannitol 50, Microcrystalline Cellulose 50, Croscarmellose Sodium 2, Magnesium Stearate 0.9 |
|  | Solvent | Water 22 (21.2%) | Water 20 (24.3%) |
|  | Acidifier | \ | 5% Aqueous HCl solution 3 (molar ratio of it to Risperidone is 1.69) |
|  | Alkalizer | \ | 10% Aqueous glycocoll solution 2.6 (the value of fomula 1 is 0.84) |
|  | Preparation Technology | Grind risperidone and then make it pass through 100 mesh sieve; homogeneously mix it with microcrystalline cellulose, mannitol and croscarmellose sodium, add water and then carry out stirring granulation, finish granule after drying wet granules, add magnesium stearate and then press. | Mix and stir risperidone and 5% aqueous HCl solution, add water and stir to form medicated acid liquid, homogeneously mix mannitol, microcrystalline cellulose, aqueous glycocoll solution and croscarmellose sodium, add the above medicated acid liquid, carry out stirring granulation, finish granule after drying wet granules, add magnesium stearate and then press. |
| Coating | Materials | Premix of film-coating (Gastric soluble opadry) 4.7, Water 20 |  |
|  | Preparation Technology | Stir when adding opadry powder in water, and continue to stir for 45 mins after adding to make the coating solution, and carry out film-coating on the tablet core. |  |

EXAMPLES 19 AND 20

Prescription and Preparation Method of Risperidone Tablets (1 mg/tablet)

|  |  | Example 19 | Example 20 |
|---|---|---|---|
| Tablet core | Drug | Risperidone 1 (1.0%, without pretreatment) | Risperidone 1 (0.9%, without pretreatment) |
|  | Adjuvant | Mannitol 50, Microcrystalline Cellulose 50, Croscarmellose Sodium 2, Magnesium Stearate 0.9 | Mannitol 50, Microcrystalline Cellulose 50, Croscarmellose Sodium 2, Magnesium Stearate 0.9, Sodium Dodecyl Sulfate 1.5 |
|  | Solvent | Water 20 (24.7%) | Water 20 (24.3%) |
|  | Acidifier | 5% Aqueous HCl solution 1.8 (molar ratio of it to Risperidone is 1.01) | 5% Aqueous HCl solution 1.8 (molar ratio of it to Risperidone is 1.01) |
|  | Alkalizer | 5% Aqueous glycocoll solution 4.1 (the value of formula 1 is 1.11) | 5% Aqueous glycocoll solution 4.1 (the value of fomula 1 is 1.11) |
|  | Preparation Technology | Mix and stir risperidone and 5% aqueous HCl solution, add water and then stir to dissolve to form medicated acid liquid, homogeneously mix mannitol, microcrystalline cellulose and croscarmellose sodium, add the above medicated acid liquid, and then mix it with aqueous glycocoll solution, carry out stirring granulation, finish granule after drying wet granules, add magnesium stearate and then press. | Mix and stir risperidone and 5% aqueous HCl solution, add water and then stir to dissolve, add sodium dodecyl sulfate and ⅓ amount of mannitol to form medicated acid liquid, homogeneously mix the left mannitol, microcrystalline cellulose and croscarmellose sodium, add the above medicated acid liquid, and then mix it with aqueous glycocoll solution, carry out stirring granulation, finish granule after drying wet granules, add magnesium stearate and then press. |
| Coating | Materials | Premix of film-coating (Gastric soluble opadry) 4.7, Water 20 | |
|  | Preparation Technology | Stir when adding opadry powder in water, and continue to stir for 45 mins after adding to make the coating solution, and carry out film-coating on the tablet core. | |

CONTRASTIVE EXAMPLE 8 AND EXAMPLE 21

Prescription and Preparation Method of Dipyridamole Tablets (25 mg/tablet)

|  | Contrastive Example 8 | Example 21 |
|---|---|---|
| Drug | Dipyridamole 25 (15.5%, sieved by 100 mesh sieve) | Dipyridamole 25 (15%, without pretreatment) |
| Adjuvant | Lactose 60, Microcrystalline Cellulose 70, Crosslinked Polyvinylpyrrolidone 3, Povidone K30 2, Magnesium Stearate 0.6, Colloidal Silicon Dioxide 0.3 Water 80 | Lactose 60, Microcrystalline Cellulose 70, Crosslinked Polyvinylpyrrolidone 3, Povidone K30 2, Magnesium Stearate 0.6, Colloidal Silicon Dioxide 0.3 Water 40 (56.3%) |
| Acidifier | / | 5% Aqueous HCl solution 40 (molar ratio of it to Dipyridamole is 1.11) |
| Alkalizer | / | 10% Aqueous NaOH solution 15 (the value of fomula 1 is 0.68) |
| Preparation Technology | Grind dipyridamole by pulverizer and then make it pass through 100 mesh sieve; homogeneously mix it with microcrystalline cellulose, lactose and crosslinked polyvinylpyrrolidone, and make povidone K30 and water into granulating liquid, add lactose, microcrystalline cellulose into fluidized spray granulator, carry out fluidized spray granulation; after finishing granule, add crosslinked polyvinylpyrrolidone, magnesium stearate and colloidal silicon dioxide and then press. | Mix dipyridamole and povidone K30, add 5% diluted HCl and then mix and stir, add water and then stir to dissolve, stir when adding 10% aqueous NaOH solution to form granulating liquid, add lactose, microcrystalline cellulose into fluidized spray granulator, carry out fluidized spray granulation; after finishing granule, add crosslinked polyvinylpyrrolidone, magnesium stearate and colloidal silicon dioxide and then press. |

EXAMPLE 22

Prescription and Preparation Method of Aripiprazole Tablets (5 mg/tablet)

| | |
|---|---|
| Drug | Aripiprazole 5 (4.4%, without pretreatment) |
| Adjuvant | Lactose 60, Microcrystalline Cellulose 40, Carboxymethyl Starch Sodium 6, Tween-80 0.5, Colloidal Silicon Dioxide 0.2, Sodium Octadecyl Fumarate 0.8 |
| Solvent | Ethanol 24 (20.9%) |
| Acidifier | Citric Acid Monohydrate 1.9 (molar ratio of it to Aripiprazole is 0.81) |
| Alkalizer | Sodium Citrate Dihydrate 0.27 (the value of fomula 1 is 0.1) |
| Preparation Technology | Dissolve aripiprazole, citric acid and tween-80 into ethanol, heat them with a water bath at about 55° C., stir to dissolve to prepare medicated acid liquid, stir and homogeneously mix lactose, microcrystalline cellulose, 50% amount of |

-continued carboxymethyl starch sodium and sodium citrate, add the above solution, stir and made into soft material, carry out extrusion granulation, finish granule after drying wet granules, add colloidal silicon dioxide, sodium octadecyl fumarate and 50% amount of carboxymethyl starch sodium, homogeneously mix and then press.

EXAMPLES 23

10

Prescription and Preparation Method of Aripiprazole Tablets (5 mg/tablet)

| | |
|---|---|
| Drug | Aripiprazole 5 (4.3%, without pretreatment) |
| Adjuvant | Mannitol 60, Microcrystalline Cellulose 40, Crosslinked Polyvinylpyrrolidone 6, Sodium Dodecyl Sulfate 1, Magnesium Stearate 0.9 |
| Solvent | 50% Aqueous ethanol solution 22 (18.8%) |
| Acidifier | Citric Acid Monohydrate 3.0 (molar ratio of it to Aripiprazole is 1.28) |
| Alkalizer | Sodium Citrate Dihydrate 1.0 (the value of fomula 1 is 0.24) |
| Preparation Technology | Add aripiprazole, citric acid and sodium dodecyl sulfate into 50% aqueous ethanol solution, heat them with a water bath at about 60° C., stir to dissolve to prepare medicated acid liquid, homogeneously mix mannitol, microcrystalline cellulose and sodium citrate, add the medicated acid liquid and carry out stirring granulation, finish granule after drying wet granules, add magnesium stearate and crosslinked polyvinylpyrrolidone, homogeneously mix and then press. |

EXAMPLE 24

30

Prescription and Preparation Method of Aripiprazole Tablets (5 mg/tablet)

| | |
|---|---|
| Drug | Aripiprazole 5 (4.5%, without pretreatment) |
| Adjuvant | Mannitol 60, Microcrystalline Cellulose 40, Carboxymethyl Starch Sodium 6, Magnesium Stearate 0.9 |
| Solvent | 60% Aqueous ethanol solution 20 (29.3%) |
| Acidifier | 5% Aqueous HCl solution 8.5 (molar ratio of it to Aripiprazole is 1.04) |
| Alkalizer | 5% Aqueous NaOH solution 4.6 (the value of fomula 1 is 0.49) |
| Preparation Technology | Add aripiprazole and 5% aqueous HCl solution into 60% aqueous ethanol solution, heat them with a water bath at about 50° C., stir to dissolve to prepare medicated acid liquid, stir when adding 5% aqueous NaOH solution into the medicated acid liquid, homogeneously mix mannitol, microcrystalline cellulose and 70% amount of carboxymethyl starch sodium, add the above solution and carry out stirring granulation, finish granule after drying wet granules, add magnesium stearate and and the left 30% amount of carboxymethyl starch sodium, homogeneously mix and then press. |

EXAMPLE 25

50

Prescription and Preparation Method of Aripiprazole Tablets (5 mg/tablet)

| | |
|---|---|
| Drug | Aripiprazole 5 (4.5%, without pretreatment) |
| Adjuvant | Lactose 70, Microcrystalline Cellulose 30, Carboxymethyl Starch Sodium 6, Magnesium Stearate 0.9 |
| Solvent | 75% Aqueous ethanol solution 24 (31.6%) |
| Acidifier | 5% Aqueous HCl solution 9 (molar ratio of it to Aripiprazole is 1.11) |
| Alkalizer | 2% Aqueous NaOH solution 2.4 (the value of fomula 1 is 0.11) |
| Preparation Technology | Dissolve aripiprazole and 5% aqueous HCl solution into 75% aqueous ethanol solution, heat them with a water bath at about 50° C., stir to dissolve to prepare medicated acid liquid, stir when adding 2% aqueous NaOH solution into the medicated acid liquid, homogeneously mix lactose, 70% amount of carboxymethyl starch sodium and microcrystalline cellulose, add the above |

-continued solution and carry out stirring granulation, finish granule after drying wet granules, add magnesium stearate and the left 30% amount of carboxymethyl starch sodium, homogeneously mix and then press.

EXAMPLE 26

Prescription and Preparation Method of Aripiprazole Tablets (5 mg/tablet) 10

| | |
|---|---|
| Drug | Aripiprazole 5 (4.3%, without pretreatment) |
| Adjuvant | Lactose 60, Microcrystalline Cellulose 40, Carboxymethyl Starch Sodium 6, Tween-80 0.25, Colloidal Silicon Dioxide 0.2, Sodium octadecyl fumarate 0.8 |
| Solvent | 75% Aqueous ethanol solution 24 (20.5%) |
| Acidifier | Citric Acid Monohydrate 1.9 (molar ratio of it to Aripiprazole is 0.81) |
| Alkalizer | Sodium Citrate Dihydrate 2.7 (the value of fomula 1 is 1.02) |
| Preparation Technology | Dissolve aripiprazole, citric acid and tween-80 into 75% aqueous ethanol solution, heat them with a water bath at about 55° C., stir to dissolve, add 20% amount of lactose to prepare medicated acid liquid, stir and homogeneously mix the left lactose, microcrystalline cellulose, 50% amount of carboxymethyl starch sodium and sodium citrate, add the above medicated acid liquid, stir and made into soft material, carry out extrusion granulation, finish granule after drying wet granules, add colloidal silicon dioxide, sodium octadecyl fumarate and 50% amount of carboxymethyl starch sodium, homogeneously mix and then press. |

EXAMPLE 27

Prescription and Preparation Method of Aripiprazole Tablets (5 mg/tablet) 30

| | |
|---|---|
| Drug | Aripiprazole 5 (4.5%, without pretreatment) |
| Adjuvant | Mannitol 80, Microcrystalline Cellulose 20, Carboxymethyl Starch Sodium 6, Magnesium Stearate 0.9 |
| Solvent | 75% Aqueous ethanol solution 22 (26.2%) |
| Acidifier | 10% Aqueous HCl solution 3.6 (molar ratio of it to Aripiprazole is 0.88) |
| Alkalizer | 10% Aqueous NaOH solution 4.3 (the value of fomula 1 is 1.09) |
| Preparation Technology | Put aripiprazole and 10% aqueous HCl solution into 75% aqueous ethanol solution, heat them with a water bath at about 50° C., stir to dissolve, stir when adding 30% amount of mannitol to prepare medicated acid liquid, homogeneously mix 10% aqueous NaOH solution, microcrystalline cellulose, 70% amount of mannitol and 70% amount of carboxymethyl starch sodium, add the above mixture, stir and made into soft material, carry out extrusion granulation, finish granule after drying wet granules, add magnesium stearate and the left 30% amount of carboxymethyl starch sodium, homogeneously mix and then press. |

EXAMPLE 28

Prescription and Preparation Method of Aripiprazole Tablets (10 mg/tablet) 50

| | |
|---|---|
| Drug | Aripiprazole 10 (7.2%, without pretreatment) |
| Adjuvant | Lactose 80, Microcrystalline Cellulose 40, Carboxymethyl Starch Sodium 6, Magnesium Stearate 0.6 |
| Solvent | 50% Aqueous ethanol solution 30 (21.5%) |
| Acidifier | DL-Malic Acid 2.4 (molar ratio of it to Aripiprazole is 0.80) |
| Alkalizer | $Na_2CO_3$ 0.28 (the value of formula 1 is 0.30) |
| Preparation Technology | Add aripiprazole and DL-Malic acid into 50% aqueous ethanol solution, heat them with a water bath at about 50° C., stir to dissolve to prepare medicated acid liquid. Dissolve $Na_2CO_3$ in appropriate water, add lactose, microcrystalline cellulose and 70% amount of carboxymethyl starch sodium and homogeneously mix, and add the above medicated acid liquid and carry out stirring granulation, finish granule after drying wet granules, add |

-continued

| | |
|---|---|
| | magnesium stearate and the left 30% amount of carboxymethyl starch sodium, homogeneously mix and then press. |

EXAMPLE 29

Prescription and Preparation Method of Aripiprazole Tablets (5 mg/tablet)

| | |
|---|---|
| Drug | Aripiprazole 5 (4.4%, without pretreatment) |
| Adjuvant | Sucrose 70, Microcrystalline Cellulose 30, Crosslinked Polyvinylpyrrolidone 6, Magnesium Stearate 0.6 |
| Solvent | 40% Aqueous ethanol solution 20 (25.7%) |
| Acidifier | 5% Aqueous HCl solution 9 (molar ratio of it to Aripiprazole is 1.11) |
| Alkalizer | Glycocoll 1.29 (the value of fomula 1 is 1.39) |
| Preparation Technology | Dissolve aripiprazole, 5% aqueous HCl solution into 40% aqueous ethanol solution, heat them with a water bath at about 60° C., stir to dissolve, add 70% amount of sucrose and stir to prepare medicated acid liquid. Dissolve glycocoll in appropriate water, homogeneously mix with 30% amount of sucrose and microcrystalline cellulose to form a mixture. Add the mixture into the medicated acid liquid, carry out stirring granulation, finish granule after drying wet granules, add magnesium stearate and crosslinked polyvinylpyrrolidone, homogeneously mix and then press. |

EXAMPLE 30

Prescription and Preparation Method of Aripiprazole Tablets (5 mg/tablet)

| | |
|---|---|
| Drug | Aripiprazole 5 (4.5%, without pretreatment) |
| Adjuvant | Sucrose 70, Microcrystalline Cellulose 30, Crosslinked Polyvinylpyrrolidone 6, Magnesium Stearate 0.6 |
| Solvent | 40% Aqueous ethanol solution 20 (25.9%) |
| Acidifier | 5% Aqueous HCl solution 9 (molar ratio of it to Aripiprazole is 1.11) |
| Alkalizer | Sodium Citrate Dihydrate 0.35 (the value of fomula 1 is 0.10) |
| Preparation Technology | Dissolve aripiprazole, 5% aqueous HCl solution in 40% aqueous ethanol solution, heat them with a water bath at about 60° C., stir to dissolve to prepare medicated acid liquid, dissolve sodium citrate in appropriate water, add sucrose, microcrystalline cellulose and homogeneously mix, and add the above medicated acid liquid, carry out stirring granulation, finish granule after drying wet granules, add magnesium stearate and crosslinked polyvinylpyrrolidone, homogeneously mix and then press. |

EXAMPLE 31

Prescription and Preparation Method of Aripiprazole Tablets (5 mg/tablet)

| | |
|---|---|
| Drug | Aripiprazole 5 (3.6%, without pretreatment) |
| Adjuvant | Lactose 60, Sucrose 20, Tween-80 0.5, Microcrystalline Cellulose 40, Crosslinked Polyvinylpyrrolidone 10, Magnesium Stearate 1 |
| Solvent | Ethanol 15 (10.7%) |
| Acidifier | Citric Acid Monohydrate 1.8 (molar ratio of it to Aripiprazole is 0.77) |
| Alkalizer | Sodium Citrate Dihydrate 2.4 (the value of fomula 1 is 0.95) |
| Preparation Technology | Mix aripiprazole, Tween-80, citric acid and ethanol, add sucrose and homogeneously mix to form medicated acid liquid, homogeneously mix lactose, microcrystalline cellulose, 50% amount of crosslinked polyvinylpyrrolidone and sodium citrate, add the above medicated acid liquid and carry out stirring granulation, finish granule after drying wet granules, add magnesium stearate and 50% amount of crosslinked polyvinylpyrrolidone, homogeneously mix and then press. |

EXAMPLE 32

Prescription and Preparation Method of Aripiprazole Orally Disintegrating Tablets (5 mg/tablet)

| | |
|---|---|
| Drug | Aripiprazole 5 (3.1%, without pretreatment) |
| Adjuvant | Mannitol 120, Microcrystalline Cellulose 25, Crosslinked Polyvinylpyrrolidone 10, Sodium Dodecyl Sulfate 0.3, Aspartame 0.8, Sodium octadecyl fumarate 1.2, Colloidal Silicon Dioxide 0.3 |
| Solvent | 95% Aqueous ethanol solution 18 (15.0%) |
| Acidifier | 10% Aqueous HCl solution 4.1 (molar ratio of it to Aripiprazole is 1.01) |
| Alkalizer | 0.2% Aqueous NaOH solution 2.3 (the value of fomula 1 is 0.01) |
| Preparation Technology | Disperse aripiprazole and sodium dodecyl sulfate in 95% aqueous ethanol solution, add 10% aqueous HCl solution, heat them with a water bath at about 65° C., stir to dissolve, add 40% amount of mannitol to prepare medicated acid liquid. Homogeneously mix 60% amount of mannitol, aspartame, microcrystalline cellulose and 0.2% aqueous NaOH solution to prepare mixed powder, mix the mixed powder and the medicated acid liquid to made into soft material, carry out extrusion granulation, finish granule after drying wet granules, add colloidal silicon dioxide, sodium octadecyl fumarate and crosslinked polyvinylpyrrolidone, homogeneously mix and then press. |

EXAMPLE 33

Prescription and Preparation Method of Aripiprazole Orally Disintegrating Tablets (10 mg/tablet)

| | |
|---|---|
| Drug | Aripiprazole 10 (4.4%, without pretreatment) |
| Adjuvant | Mannitol 140, Microcrystalline Cellulose 50, Crosslinked Polyvinylpyrrolidone 10, Aspartame 1, Magnesium Stearate 0.9 |
| Solvent | 30% Aqueous ethanol solution 20 (8.9%) |
| Acidifier | Citric Acid Monohydrate 4.7 (molar ratio of it to Aripiprazole is 1.00) |
| Alkalizer | Sodium Citrate Dihydrate 8.6 (the value of fomula 1 is 1.31) |
| Preparation Technology | Dissolve aripiprazole and citric acid monohydrate in 30% aqueous ethanol solution, heat them with a water bath at about 65° C., stir to dissolve to prepare medicated acid liquid. Stir and homogeneously mix mannitol, microcrystalline cellulose, aspartame and sodium citrate, add the above solution, stir and made into soft material, carry out extrusion granulation, finish granule after drying wet granules, add magnesium stearate and crosslinked polyvinylpyrrolidone, homogeneously mix and then press. |

EXAMPLE 34

Prescription and Preparation Method of Aripiprazole Capsules (5 mg/tablet)

| | |
|---|---|
| Drug | Aripiprazole 5 (4.2%, without pretreatment) |
| Adjuvant | Lactose 76, Microcrystalline Cellulose 30, Carboxymethyl Starch Sodium 6, Magnesium Stearate 0.9 |
| Solvent | 95% Aqueous ethanol solution 20 (26.1%) |
| Acidifier | 5% Aqueous HCl solution 11 (molar ratio of it to Aripiprazole is 1.35) |
| Alkalizer | $Na_2CO_3$ 0.8 (the value of fomula 1 is 1.00) |
| Preparation Technology | Add aripiprazole and 5% aqueous HCl solution into 95% aqueous ethanol solution, stir to dissolve to prepare medicated acid liquid, homogeneously mix $Na_2CO_3$, lactose, microcrystalline cellulose and 70% amount of carboxymethyl starch sodium, add the medicated acid liquid, stir and made into soft material, carry out extrusion granulation, finish granule after drying wet granules, add magnesium stearate and the left 30% amount of carboxymethyl starch sodium, homogeneously mix and then capsule them. |

EXAMPLE 35

Prescription and Preparation Method of Aripiprazole
Capsules (5 mg/tablet)

| | |
|---|---|
| Drug | Aripiprazole 5 (4.2%, without pretreatment) |
| Adjuvant | Lactose 76, Microcrystalline Cellulose 30, Carboxymethyl Starch Sodium 6, Magnesium Stearate 0.9 |
| Solvent | 95% Aqueous ethanol solution 20 (26.3%) |
| Acidifier | 5% Aqueous HCl solution 11 (molar ratio of it to Aripiprazole is 1.35) |
| Alkalizer | $Na_2CO_3$ 0.16 (the value of fomula 1 is 0.20) |
| Preparation Technology | Add aripiprazole and 5% aqueous HCl solution into 95% aqueous ethanol solution, stir to dissolve to prepare medicated acid liquid, homogeneously mix with lactose, microcrystalline cellulose and 70% amount of carboxymethyl starch sodium, then mix with $Na_2CO_3$ which dissolves in a little water, stir and made into soft material, carry out extrusion granulation, finish granule after drying wet granules, add magnesium stearate and the left 30% amount of carboxymethyl starch sodium, homogeneously mix and then capsule them. |

EXAMPLE 36

Prescription and Preparation Method of Eszopiclone
Tablets (2 mg/tablet)

| | | |
|---|---|---|
| Tablet Core | Drug | Eszopiclone 2 (2.9%, without pretreatment) |
| | Adjuvant | Sucrose 25, Microcrystalline Cellulose 30, Starch 5, Carboxymethyl Starch Sodium 2, Povidone K30 1, Polyethyleneglycol-6000 1, Magnesium Stearate 0.3 |
| | Solvent | Water 8, 95% Aqueous ethanol solution 4 (17.6%) |
| | Acidifier | L-Tartaric Acid 0.8 (molar ratio of it to Eszopiclone is 1.04) |
| | Alkalizer | L-Sodium Tartrate Dihydrate 1 (the value of formula 1 is 0.82) |
| | Preparation Technology | Make eszopiclone, polyethyleneglycol-6000, povidone K30, tartaric acid, 95% aqueous ethanol solution and water into medicated acid liquid, homogeneously mix sucrose, microcrystalline cellulose, starch, carboxymethyl starch sodium and sodium tartrate, add the medicated acid liquid, stir and made into soft material, carry out extrusion granulation, finish granule after drying wet granules, add magnesium stearate, homogeneously mix and then press. |
| Coating | Materials | Premix of film-coating (Gastric soluble opadry) 2.4, Water 10 |
| | Preparation Technology | Stir when adding opadry powder in water, and continue to stir for 45 mins after adding to make the coating solution, and carry out film-coating on the tablet core. |

EXAMPLE 37

Prescription and Preparation Method of Eszopiclone
Tablets (1 mg/tablet)

| | | |
|---|---|---|
| Tablet Core | Drug | Eszopiclone1(1.5%, without pretreatment) |
| | Adjuvant | Lactose 40, Microcrystalline Cellulose 20, Carboxymethyl Starch Sodium 2.5, Hypromellose 0.5, Magnesium Stearate 0.3 |
| | Solvent | Water 11(16.6%) |
| | Acidifier | Citric Acid Monohydrate 0.65 (molar ratio of it to Eszopiclone is 1.2) |
| | Alkalizer | Sodium Citrate Dihydrate 1.14(the value of fomula 1 is 1.25) |
| | Preparation Technology | Disperse hypromellose by 80° C. hot water, add water and stir to dissolve, and make it, eszopiclone, citric acid and the left water into medicated acid liquid, homogeneously mix lactose, microcrystalline cellulose, ⅔ amount of carboxymethyl starch sodium and sodium citrate, add the medicated acid liquid and carry out stirring granulation, finish granule after drying wet granules, add magnesium stearate and ⅓ amount of carboxymethyl starch sodium, homogeneously mix and then press. |
| Coating | Materials | Premix of film-coating (Gastric soluble opadry) 2.5, Water 11 |
| | Preparation | Stir when adding opadry powder in water, and continue to stir for |

-continued

| | Technology | 45 mins after adding to make the coating solution, and carry out film-coating on the tablet core. |

EXAMPLE 38

Prescription and Preparation Method of Eszopiclone Tablets (6 mg/tablet)

| Tablet Core | Drug | Eszopiclone 6 (10.2%, without pretreatment) |
|---|---|---|
| | Adjuvant | Lactose 30, Microcrystalline Cellulose 20, Povidone K30 2, Magnesium Stearate 0.25, Colloidal Silicon Dioxide 0.15 |
| | Solvent | Water 19 (49.8%) |
| | Acidifier | 5% Aqueous HCl solution 11 (molar ratio of it to Eszopiclone is 0.98) |
| | Alkalizer | $Na_2CO_3$ 0.16 (the value of fomula 1 is 0.2) |
| | Preparation Technology | Make eszopiclone, povidone K30, 5% aqueous HCl solution and water into medicated acid liquid, stir when adding $Na_2CO_3$ solution (dissolved in a little water) to form granulating liquid. Add lactose, microcrystalline cellulose into fluidized spray granulator, carry out fluidized spray granulation; after finishing granule, add magnesium stearate and colloidal silicon dioxide, and homogeneously mix and then press. |
| Coating | Materials | Hypromellose 2, Polyethyleneglycol-6000 0.4, Titanium Dioxide 0.5, Water 17 |
| | Preparation Technology | Disperse hypromellose by 80° C. hot water, then add water and stir to dissolve, add polyethyleneglycol-6000 and homogenized titanium dioxide to prepare the coating solution, and carry out film-coating on the tablet core. |

EXAMPLE 39

Prescription and Preparation Method of Eszopiclone Tablets (1 mg/tablet)

| Tablet Core | Drug | Eszopiclone 1 (0.2%, without pretreatment) |
|---|---|---|
| | Adjuvant | Lactose 340, Microcrystalline Cellulose 150, Carboxymethyl Starch Sodium 7.5, Povidone K30 5, Magnesium Stearate 3, Colloidal Silicon Dioxide 1.5 |
| | Acidifier | 5% Aqueous HCl solution 1.6 (molar ratio of it to Eszopiclone is 0.85) |
| | Alkalizer | $Na_2CO_3$ 0.09 (the value of fomula 1 is 0.77) |
| | Solvent | Water 90, 95% Aqueous ethanol solution 20 (21.7%) |
| | Preparation Technology | Make eszopiclone, povidone K30, tartaric acid, 95% aqueous ethanol solution and 50% amount of water into medicated acid liquid. Make $Na_2CO_3$ and 50% amount of water into solution. Homogeneously mix lactose, microcrystalline cellulose, ⅔ amount of carboxymethyl starch sodium, add the solution of $Na_2CO_3$ and stir for a period, stir when adding the medicated acid liquid and continue stirring and made into soft material, carry out extrusion granulation, finish granule after drying wet granules, add magnesium stearate, colloidal silicon dioxide and ⅓ amount of carboxymethyl starch sodium, homogeneously mix and then press. |
| Coating | Materials | Premix of film-coating (Gastric soluble opadry) 20, Water 85 |
| | Preparation Technology | Stir when adding opadry powder in water, and continue to stir for 45 mins after adding to make the coating solution, and carry out film-coating on the tablet core. |

EXAMPLE 40

Prescription and Preparation Method of Eszopiclone Tablets (1 mg/tablet)

| | | |
|---|---|---|
| Tablet Core | Drug | Eszopiclone 1 (1.6%, without pretreatment) |
| | Adjuvant | Lactose 20, Microcrystalline Cellulose 20, Maltitol 20, Polyethyleneglycol-6000 1, Magnesium Stearate 0.4, Colloidal Silicon Dioxide 0.2 |
| | Solvent | Water 11, 95% Aqueous ethanol solution 20 (52.1%) |
| | Acidifier | 5% Aqueous HCl solution 2 (molar ratio of it to Eszopiclone is 1.06) |
| | Alkalizer | Disodium Hydrogen Phosphate Dodecahydrate 0.5 (the value of formula 1 is 1.02) |
| | Preparation Technology | Mix eszopiclone, polyethyleneglycol-6000, 5% aqueous HCl solution and water to form solution, add 45% amount of maltitol and stir to form medicated acid liquid, homogeneously mix lactose, microcrystalline cellulose and 55% amount of maltitol, add the medicated acid liquid, carry out stirring granulation, stir when adding disodium hydrogen phosphate solution (dissolving disodium hydrogen phosphate in a little water) and continue stirring granulation, finish granule after drying wet granules, add magnesium stearate and colloidal silicon dioxide, homogeneously mix and then press. |
| Coating | Materials | Premix of film-coating (Gastric soluble opadry) 3, Water 13 |
| | Preparation Technology | Stir when adding opadry powder in water, and continue to stir for 45 mins after adding to make the coating solution, and carry out film-coating on the tablet core. |

EXAMPLE 41

Prescription and Preparation Method of Eszopiclone Tablets (2 mg/tablet)

| | | |
|---|---|---|
| Tablet Core | Drug | Eszopiclone 2 (3.2%, without pretreatment) |
| | Adjuvant | Mannitol 25, Microcrystalline Cellulose 30, Poloxamer 1, Magnesium Stearate 0.3, Colloidal Silicon Dioxide 0.2, Crospovidone 2 |
| | Solvent | Water 11 (17.7%) |
| | Acidifier | DL-Malic Acid 0.65 (molar ratio of it to Eszopiclone is 0.94) |
| | Alkalizer | Sodium DL-malate trihydrate 1.12 (the value of fomula 1 is 1) |
| | Preparation Technology | Make eszopiclone, poloxamer, DL-malic acid and water into medicated acid liquid, homogeneously mix mannitol and microcrystalline cellulose, add the medicated acid liquid and srir, stir when adding sodium DL-malate trihydrate solution (dissolving sodium DL-malate trihydrate in a little water) and continue stirring granulation, finish granule after drying wet granules, add magnesium stearate, crospovidone and colloidal silicon dioxide, homogeneously mix and then press. |
| Coating | Materials | Premix of film-coating (Gastric soluble opadry) 2.2, Water 10 |
| | Preparation Technology | Stir when adding opadry powder in water, and continue to stir for 45 mins after adding to make the coating solution, and carry out film-coating on the tablet core. |

EXAMPLE 42

Prescription and Preparation Method of Eszopiclone Tablets (2 mg/tablet)

| | | |
|---|---|---|
| Tablet Core | Drug | Eszopiclone 2 (3.5%, without pretreatment) |
| | Adjuvant | Lactose 30, Microcrystalline Cellulose 20, Polyethyleneglycol-6000 1, Carboxymethyl Starch Sodium 3, Magnesium Stearate 0.3, Colloidal Silicon Dioxide 0.15 |
| | Solvent | Water 11(19.1%) |
| | Acidifier | DL-Malic Acid 0.8 (molar ratio of it to Eszopiclone is 1.16) |
| | Alkalizer | $Na_2CO_3$ 0.25 (the value of fomula 1 is 0.8) |
| | Preparation | Make eszopiclone, polyethyleneglycol-6000, DL-malic acid and |

-continued

| | Technology | water into medicated acid liquid, homogeneously mix lactose, microcrystalline cellulose and ⅔ amount of carboxymethyl starch sodium, add the medicated acid liquid and stir, stir when adding Na₂CO₃ solution (dissolving Na₂CO₃ in a little water) and continue stirring granulation, finish granule after drying wet granules, add magnesium stearate, ⅓ amount of carboxymethyl starch sodium and colloidal silicon dioxide, homogeneously mix and then press. |
|---|---|---|
| Coating | Materials Preparation Technology | Premix of film-coating (Gastric soluble opadry) 2.1, Water 9 Stir when adding opadry powder in water, and continue to stir for 45 mins after adding to make the coating solution, and carry out film-coating on the tablet core. |

EXAMPLE 43

Eszopiclone Tablets (2 mg/tablet)

| Tablet Core | Drug | Eszopiclone 2 (2.0%, without pretreatment) |
|---|---|---|
| | Adjuvant | Lactose 60, Microcrystalline Cellulose 30, Carboxymethyl Starch Sodium 2.5, Crospovidone 5, Magnesium Stearate 0.6, Colloidal Silicon Dioxide 0.2 |
| | Solvent | 95% Aqueous ethanol solution 14 (19.0%) |
| | Acidifier | 5% Aqueous HCl solution 2.7 (molar ratio of it to Eszopiclone is 0.72) |
| | Alkalizer | 5% Aqueous NaOH solution 2.7 (the value of fomula 1 is 0.91) |
| | Preparation Technology | Make eszopiclone, 95% aqueous ethanol solution and 5% aqueous HCl solution into medicated acid liquid. Homogeneously mix 5% aqueous NaOH solution, lactose, microcrystalline cellulose and crospovidone, add the medicated acid liquid and carry out stirring granulation, finish granule after drying wet granules, add magnesium stearate, colloidal silicon dioxide and carboxymethyl starch sodium, homogeneously mix and then press. |
| Coating | Materials Preparation Technology | Premix of film-coating (Gastric soluble opadry) 4.5, Water 19 Stir when adding opadry powder in water, and continue to stir for 45 mins after adding to make the coating solution, and carry out film-coating on the tablet core. |

EXAMPLE 44

Eszopiclone Tablets (2 mg/tablet)

| Tablet Core | Drug | Eszopiclone 2 (2.0%, without pretreatment) |
|---|---|---|
| | Adjuvant | Lactose 60, Microcrystalline Cellulose 30, Carboxymethyl Starch Sodium 2.5, Sodium Dodecyl Sulfate 0.1, Sodium Octadecyl Fumarate 0.8, Talcum Powder 2 |
| | Solvent | Water 14 (18.1%) |
| | Acidifier | 5% Aqueous HCl solution 3.95 (molar ratio of it to Eszopiclone is 1.05) |
| | Alkalizer | Glycocoll 0.61 (the value of fomula 1 is 1.5) |
| | Preparation Technology | Make eszopiclone, sodium dodecyl sulfate, water and 5% aqueous HCl solution into medicated acid liquid. Homogeneously mix lactose, microcrystalline cellulose and glycocoll, add the medicated acid liquid and carry out stirring granulation, finish granule after drying wet granules, add sodium octadecyl fumarate, talcum powder and carboxymethyl starch sodium, homogeneously mix and then press. |
| Coating | Materials Preparation Technology | Premix of film-coating (Gastric soluble opadry) 4.5, Water 19 Stir when adding opadry powder in water, and continue to stir for 45 mins after adding to make the coating solution, and carry out film-coating on the tablet core. |

EXAMPLE 45

Prescription and Preparation Method of Eszopiclone Tablets (1 mg/tablet)

| Tablet Core | Drug | Eszopiclone 1 (1.5%, without pretreatment) |
|---|---|---|
| | Adjuvant | Lactose 40, Starch 20, Carboxymethyl Starch Sodium 1, Sucrose 2, Magnesium Stearate 0.3, Colloidal Silicon Dioxide 0.1 |
| | Solvent | Water 12 (21.3%) |
| | Acidifier | 5% Aqueous HCl solution 2 (molar ratio of it to Eszopiclone is 1.07) |
| | Alkalizer | Sodium Citrate Dihydrate 0.8 (the value of fomula 1 is 0.99) |
| | Preparation Method | Make eszopiclone, sucrose, 5% aqueous HCl solution and water into medicated acid liquid, homogeneously mix lactose, starch, carboxymethyl starch sodium and sodium citrate dihydrate, add the medicated acid liquid and carry out stirring granulation, finish granule after drying wet granules, add magnesium stearate and colloidal silicon dioxide, homogeneously mix and then press. |
| Coating | Materials | Premix of film-coating (Gastric soluble opadry) 2.5, Water 11 |
| | Preparation Technology | Stir when adding opadry powder in water, and continue to stir for 45 mins after adding to make the coating solution, and carry out film-coating on the tablet core. |

EXAMPLE 46

Prescription and Preparation Method of Eszopiclone Tablets (2 mg/tablet)

| Tablet Core | Drug | Eszopiclone 2 (2.8%, without pretreatment) |
|---|---|---|
| | Adjuvant | Lactose 40, Microcrystalline Cellulose 25, Povidone K30 1.5, Mannitol 2, Carboxymethyl Starch Sodium 1, Colloidal Silicon Dioxide 0.2, Magnesium Stearate 0.3 |
| | Solvent | Water 13(22.9%) |
| | Acidifier | 5% Aqueous HCl solution 3.8(molar ratio of it to Eszopiclone is 1.01) |
| | Alkalizer | $Na_2CO_3$ 0.3 (the value of fomula 1 is 1.09) |
| | Preparation Technology | Make eszopiclone, mannitol, povidone K30, 5% aqueous HCl solution and water into medicated acid liquid, homogeneously mix lactose, microcrystalline cellulose and carboxymethyl starch sodium, add the medicated acid liquid and carry out mixing granulation, stir when add $Na_2CO_3$ solution (dissolving $Na_2CO_3$ in a little water) and then continue stirring granulation, finish granule after drying wet granules, add magnesium stearate and colloidal silicon dioxide, homogeneously mix and then press. |
| Coating | Materials | Premix of film-coating (Gastric soluble opadry) 3, Water 13 |
| | Preparation Technology | Stir when adding opadry powder in water, and continue to stir for 45 mins after adding to make the coating solution, and carry out film-coating on the tablet core. |

EXAMPLE 47

Prescription and Preparation Method of Zopiclone Tablets (2.5 mg/tablet)

| Tablet Core | Drug | Zopiclone 2.5 (3.0%, without pretreatment) |
|---|---|---|
| | Adjuvant | Lactose 37.5, Microcrystalline Cellulose 37.5, Povidone K30 2, Magnesium Stearate 0.5, Colloidal Silicon Dioxide 0.2 |
| | Solvent | Water 40 (48.5%) |
| | Acidifier | DL-Tartaric Acid 1 (molar ratio of it to Zopiclone is 1.04) |
| | Alkalizer | DL-Sodium Tartrate Dihydrate 1.3 (the value of fomula 1 is 0.85) |
| | Preparation Technology | Make zopiclone, povidone K30, DL-tartaric acid and water into medicated acid liquid, stir when adding DL-sodium tartrate solution (dissolved in a little water) to form granulating liquid. Add lactose, microcrystalline cellulose into fluidized spray granulator, carry out fluidized spray granulation, after finishing |

|         |                         |                                                                                                                                                                                                                                                                                                                                                                                                                                                                                                                                                   |
|---------|-------------------------|----------------------------------------------------------------------------------------------------------------------------------------------------------------------------------------------------------------------------------------------------------------------------------------------------------------------------------------------------------------------------------------------------------------------------------------------------------------------------------------------------------------------------------|
|         |                         | granule, add magnesium stearate and colloidal silicon dioxide, homogeneously mix and then press. |
| Coating | Materials               | Hypromellose 2, Polyethyleneglycol-6000 0.35, Titanium Dioxide 0.4, Water 16 |
|         | Preparation Technology  | Disperse hypromellose by 80° C. hot water, then add water and stir to dissolve, add polyethyleneglycol-6000 and homogenized titanium dioxide to make the coating solution, and carry out film-coating on the tablet core. |

EXAMPLE 48

Prescription and Preparation Method of Zopiclone Tablets (2.5 mg/tablet)

| Tablet Core | Drug | Zopiclone 2.5 (3.6%, without pretreatment) |
|---|---|---|
| | Adjuvant | Sucrose 25, Microcrystalline Cellulose 30, Starch 5, Carboxymethyl Starch Sodium 2, Povidone K30 1, Polyethyleneglycol-6000 1, Magnesium Stearate 0.3 |
| | Solvent | Water 11 (15.9%) |
| | Acidifier | Citric Acid Monohydrate 1.2 (molar ratio of it to Zopiclone is 0.89) |
| | Alkalizer | Disodium Hydrogen Phosphate Dodecahydrate 1.1 (the value of fomula 1 is 1.08) |
| | Preparation Technology | Make zopiclone, polyethyleneglycol-6000, povidone K30, citric acid and water into medicated acid liquid, homogeneously mix sucrose, microcrystalline cellulose and carboxymethyl starch sodium, add the medicated acid liquid, carry out stirring granulation, stir when adding disodium hydrogen phosphate solution (dissolving disodium hydrogen phosphate in a little water), continue stirring granulation, finish granule after drying wet granules, add magnesium stearate, homogeneously mix and then press. |
| Coating | Materials | Premix of film-coating (Gastric soluble opadry) 2.4, Water 10 |
| | Preparation Technology | Stir when adding opadry powder in water, and continue to stir for 45 mins after adding to make the coating solution, and carry out film-coating on the tablet core. |

EXAMPLE 49

Prescription and Preparation Method of Zopiclone Tablets (3 mg/tablet)

| Tablet Core | Drug | Zopiclone 3 (2.9%, without pretreatment) |
|---|---|---|
| | Adjuvant | Mannitol 60, Microcrystalline Cellulose 30, Hydroxypropylcellulose 5, Povidone K30 1, Hypromellose 0.33, Colloidal Silicon Dioxide 0.2, Magnesium Stearate 0.6 |
| | Solvent | Water 22 (21.4%) |
| | Acidifier | Citric Acid Monohydrate 1.7 (molar ratio of it to Zopiclone is 1.05) |
| | Alkalizer | Sodium Citrate Dihydrate 0.8 (the value of fomula 1 is 0.34) |
| | Preparation Technology | Disperse hypromellose by 80° C. hot water, add water and stir to dissolve, and make it, zopiclone, povidone K30, citric acid and water into medicated acid liquid, homogeneously mix mannitol, microcrystalline cellulose and hydroxypropylcellulose, add sodium citrate solution (dissolving sodium citrate in a little water) and stir, and then add the medicated acid liquid and carry out stirring granulation, finish granule after drying wet granules, add magnesium stearate and colloidal silicon dioxide, homogeneously mix and then press. |
| Coating | Materials | Premix of film-coating (gastric soluble opadry) 4, Water 18 |
| | Preparation Technology | Stir when adding opadry powder in water, and continue to stir for 45 mins after adding to make the coating solution, and carry out film-coating on the tablet core. |

EXAMPLE 50

Prescription and Preparation Method of Zopiclone Tablets (2.5 mg/tablet)

| Tablet Core | Drug | Zopiclone 2.5 (3.7%, without pretreatment) |
|---|---|---|
| | Adjuvant | Lactose 40, Sucrose 2, Starch 20, Carboxymethyl Starch Sodium 2, Magnesium Stearate 0.3, Colloidal Silicon Dioxide 0.1 |
| | Solvent | Water 12 (17.6%) |
| | Acidifier | D-Malic Acid 0.88 (molar ratio of it to Zopiclone is 1.02) |
| | Alkalizer | $Na_2CO_3$ 0.3 (the value of fomula 1 is 0.86) |
| | Preparation Technology | Make zopiclone, sucrose, D-malic acid and water into medicated acid liquid, homogeneously mix lactose, starch and $Na_2CO_3$, add the medicated acid liquid and carry out stirring granulation, finish granule after drying wet granules, add magnesium stearate and colloidal silicon dioxide, homogeneously mix and then press. |
| Coating | Materials | Premix of film-coating (Gastric soluble opadry) 2.5, Water 11 |
| | Preparation Technology | Stir when adding opadry powder in water, and continue to stir for 45 mins after adding to make the coating solution, and carry out film-coating on the tablet core. |

EXAMPLE 51

Prescription and Preparation Method of Zopiclone tablets (7.5 mg/tablet)

| Tablet Core | Drug | Zopiclone 7.5 (8.9%, without pretreatment) |
|---|---|---|
| | Adjuvant | Lactose 40, Microcrystalline Cellulose 25, Povidone K30 2, Hypromellose 0.5, Magnesium Stearate 0.25, Colloidal Silicon Dioxide 0.15 |
| | Solvent | Water 40 (47.7%) |
| | Acidifier | Citric Acid Monohydrate 4 (molar ratio of it to Zopiclone is 0.99) |
| | Alkalizer | Sodium Citrate Dihydrate 4.5 (the value of fomula 1 is 0.8) |
| | Preparation Technology | Disperse hypromellose by 80° C. hot water, add water and stir to dissolve, and make it, zopiclone, povidone K30, citric acid and water into medicated acid liquid, stir when adding sodium citrate (dissolved in a little water) to form granulating liquid, add lactose, microcrystalline cellulose into fluidized spray granulator, carry out fluidized spray granulation, after finishing granule, add magnesium stearate and colloidal silicon dioxide, homogeneously mix and then press. |
| Coating | Materials | Hypromellose 2, Polyethyleneglycol-6000 0.4, Titanium Dioxide 0.5, Water 17 |
| | Preparation Technology | Disperse hypromellose by 80° C. hot water, add water and stir to dissolve, add polyethyleneglycol-6000 and homogenized titanium dioxide to make the coating solution, and carry out film-coating on the tablet core. |

EXAMPLE 52

Prescription and Preparation Method of Zopiclone Tablets (2.5 mg/tablet)

| Tablet Core | Drug | Zopiclone 2.5 (0.5%, without pretreatment) |
|---|---|---|
| | Adjuvant | Lactose 340, Microcrystalline Cellulose 150, Carboxymethyl Starch Sodium 7.5, Povidone K30 5, Magnesium Stearate 3, Colloidal Silicon Dioxide 1.5 |
| | Solvent | 95% Aqueous ethanol solution 20, Water 200 (42.8%) |
| | Acidifier | Citric Acid Monohydrate 1.5 (molar ratio of it to Zopiclone is 1.11) |
| | Alkalizer | Sodium Citrate Dihydrate 2.5 (the value of fomula 1 is 1.19) |
| | Preparation Technology | Make zopiclone, povidone K30, citric acid, 95% aqueous ethanol solution and water into medicated acid liquid, stir when adding sodium citrate (dissolved in a little water) to form granulating liquid. Add lactose, microcrystalline cellulose and ⅔ amount of carboxymethyl starch sodium into fluidized spray granulator, carry out fluidized spray granulation; after finishing granule, add magnesium stearate, ⅓ amount of carboxymethyl starch sodium |

-continued

| | | |
|---|---|---|
| | | and colloidal silicon dioxide, homogeneously mix and then press. |
| Coating | Materials | Premix of film-coating (Gastric soluble opadry) 20, Water 85 |
| | Preparation Technology | Stir when adding opadry powder in water, and continue to stir for 45 mins after adding to make the coating solution, and carry out film-coating on the tablet core. |

EXAMPLE 53

Prescription and Preparation Method of Zopiclone Tablets (2.5 mg/tablet)

| | | |
|---|---|---|
| Tablet Core | Drug | Zopiclone 2.5 (3.9%, without pretreatment) |
| | Adjuvant | Lactose 20, Microcrystalline Cellulose 20, Maltitol 20, Polyethyleneglycol-6000 1, Sodium Octadecyl Fumarate 0.5, Colloidal Silicon Dioxide 0.2 |
| | Solvent | Water 11 (17.0%) |
| | Acidifier | 5% Aqueous HCl solution 5 (molar ratio of it to Zopiclone is 1.06) |
| | Alkalizer | $Na_2CO_3$ 0.36 (the value of fomula 1 is 0.99) |
| | Preparation Technology | Make zopiclone, polyethyleneglycol-6000, 5% aqueous HCl solution and water into medicated acid liquid, homogeneously mixing lactose, maltitol, microcrystalline cellulose and $Na_2CO_3$, add the medicated acid liquid and carry out stirring granulation, finish granule after drying wet granules, add sodium octadecyl fumarate and colloidal silicon dioxide, homogeneously mix and then press. |
| Coating | Materials | Premix of film-coating (Gastric soluble opadry) 3, Water 13 |
| | Preparation Technology | Stir when adding opadry powder in water, and continue to stir for 45 mins after adding to make the coating solution, and carry out film-coating on the tablet core. |

EXAMPLE 54

Prescription and Preparation Method of Zopiclone Tablets (2.5 mg/tablet)

| | | |
|---|---|---|
| Tablet Core | Drug | Zopiclone 2.5 (4.2%, without pretreatment) |
| | Adjuvant | Mannitol 25, Microcrystalline Cellulose 30, Poloxamer 1, Magnesium Stearate 0.3, Colloidal Silicon Dioxide 0.2 |
| | Solvent | 95% Aqueous ethanol solution 3, Water 5 (22.4%) |
| | Acidifier | 5% Aqueous HCl solution 5.6 (molar ratio of it to Zopiclone is 1.19) |
| | Alkalizer | $Na_2CO_3$ 0.2 (the value of fomula 1 is 0.49) |
| | Preparation Technology | Make zopiclone, poloxamer, 5% aqueous HCl solution, 95% aqueous ethanol solution and water into medicate acid liquid, homogeneously mix mannitol, microcrystalline cellulose and $Na_2CO_3$, add the medicated acid liquid and carry out stirring granulation, finish granule after drying wet granules, add magnesium stearate and colloidal silicon dioxide, homogeneously mix and then press. |
| Coating | Materials | Premix of film-coating (gastric soluble opadry) 2.2, Water 10 |
| | Preparation Technology | Stir when adding opadry powder in water, and continue to stir for 45 mins after adding to make thecoating solution, and carry out film-coating on the tablet core. |

EXAMPLE 55

Prescription and Preparation Method of Zopiclone Tablets (2 mg/tablet)

| | | |
|---|---|---|
| Tablet Core | Drug | Zopiclone 2 (1.6%, without pretreatment) |
| | Adjuvant | Lactose 60, Microcrystalline Cellulose 60, Carboxymethyl Starch Sodium 5, Hypromellose 0.6, Magnesium Stearate 0.75 |

|   |   |   |
|---|---|---|
|   | Solvent | Water 13(16.2%) |
|   | Acidifier | 5% Aqueous HCl solution 4 (molar ratio of it to Zopiclone is 1.06) |
|   | Alkalizer | 0.5% Aqueous NaOH solution 4 (the value of fomula 1 is 0.09) |
|   | Preparation Technology | Disperse hypromellose by 80° C. hot water, add water and stir to dissolve, and make it, zopiclone, 5% aqueous HCl solution and water into medicated acid liquid, homogeneously mix lactose, microcrystalline cellulose and ⅔ amount of carboxymethyl starch sodium, add 0.5% aqueous NaOH solution and homogeneously mix, and then add the medicated acid liquid and carry out stirring granulation, finish granule after drying wet granules, add magnesium stearate and ⅓ amount of carboxymethyl starch sodium, homogeneously mix and then press. |
| Coating | Materials | Premix of film-coating (gastric soluble opadry)5, Water 21 |
|   | Preparation Technology | Stir when adding opadry powder in water, and continue to stir for 45 mins after adding to make the coating solution, and carry out film-coating on the tablet core. |

EXAMPLE 56

Prescription and Preparation Method of Zopiclone Tablets (2.5 mg/tablet)

| Tablet Core | Drug | Zopiclone 2.5 (1.8%, without pretreatment) |
|---|---|---|
|   | Adjuvant | Lactose 60, Sucrose 5, Microcrystalline Cellulose 60, Starch 5, Crospovidone 2, Magnesium Stearate 0.8, Talcum Powder 2 |
|   | Solvent | Water 18(16.2%) |
|   | Acidifier | 5% Aqueous HCl solution 4.7 (molar ratio of it to Zopiclone is 1) |
|   | Alkalizer | Glycocoll 0.75 (the value of fomula 1 is 1.55) |
|   | Preparation Technology | Make zopiclone, sucrose, 5% aqueous HCl solution and ¾ amount of water into medicated acid liquid, stir when adding glycocoll solution (dessolved with ¼ amount of water) to form granulating liquid. Homogeneously mix lactose, microcrystalline cellulose, starch and crospovidone, add the granulating liquid and carry out stirring granulation, finish granule after drying wet granules, add magnesium stearate and talcum powder, homogeneously mix and then press. |
| Coating | Materials | Premix of film-coating (gastric soluble opadry) 5, Water 21 |
|   | Preparation Technology | Stir when adding opadry powder in water, and continue to stir for 45 mins after adding to make the coating solution, and carry out film-coating on the tablet core. |

EXAMPLE 57

Prescription and Preparation Method of Zopiclone Tablets (2.5 mg/tablet)

| Tablet Core | Drug | Zopiclone 2.5 (3.5%, without pretreatment) |
|---|---|---|
|   | Adjuvant | Lactose 40, Microcrystalline Cellulose 25, Sodium Dodecyl Sulfate 0.15, Magnesium Stearate0.25, Colloidal Silicon Dioxide 0.15 |
|   | Solvent | Water 12 (16.9%) |
|   | Acidifier | D-Tartaric Acid 0.5, Citric Acid Monohydrate 0.68 (molar ratio of it to Zopiclone is 1.02) |
|   | Alkalizer | D-Sodium Tartrate Dihydrate 0.77, Sodium Citrate Dihydrate1 (the value of fomula 1 is 1.03) |
|   | Preparation Technology | Make zopiclone, D-tartaric acid, citric acid, sodium dodecyl sulfate and water into medicated acid liquid. Homogeneously mix lactose, microcrystalline cellulose, D-sodium tartrate and sodium citrate, add the medicated acid liquid and carry out stirring granulation, finish granule after drying wet granules, add magnesium stearate and colloidal silicon dioxide, homogeneously mix and then press. |
| Coating | Materials | Premix of film-coating (gastric soluble opadry) 2.8, Water 12 |
|   | Preparation Technology | Stir when adding opadry powder in water, and continue to stir for 45 mins after adding to make the coating solution, and carry out film-coating on the tablet core. |

EXAMPLE 58

Prescription and Preparation Method of Zopiclone Tablets (2.5 mg/tablet)

| | | |
|---|---|---|
| Tablet Core | Drug | Zopiclone 2.5 (1.9%, without pretreatment) |
| | Adjuvant | Lactose 60, Microcrystalline Cellulose 60, Carboxymethyl Starch Sodium 5, Tween-80 0.13, Sodium octadecyl fumarate 0.8, Talcum Powder 2 |
| | Solvent | Water 12, 95% Aqueous ethanol solution 6 (17.3%) |
| | Acidifier | 5% Aqueous HCl solution 4.9 (molar ratio of it to Zopiclone is 1.04) |
| | Alkalizer | Sodium Citrate Dihydrate 0.6 (the value of fomula 1 is 0.31) |
| | Preparation Technology | Make zopiclone, 5% aqueous HCl solution and ⅔ amount of water, 95% aqueous ethanol solution and tween-80 into medicated acid liquid. Homogeneously mix lactose, microcrystalline cellulose, 50% amount of carboxymethyl starch sodium and sodium citrate solution (dissolved in ⅓ amount of water), add the medicated acid liquid and carry out stirring granulation, finish granule after drying wet granules, add sodium octadecyl fumarate, 50% amount of carboxymethyl starch sodium and talcum powder, homogeneously mix and then tablettig |
| Coating | Materials | Premix of film-coating (gastric soluble opadry) 5, Water 21 |
| | Preparation Technology | Stir when adding opadry powder in water, and continue to stir for 45 mins after adding to make the coating solution, and carry out film-coating on the tablet core. |

EXAMPLE 59

Prescription and Preparation Method of Zopiclone Tablets (2 mg/tablet)

| | | |
|---|---|---|
| Tablet Core | Drug | Zopiclone 2 (1.5%, without pretreatment) |
| | Adjuvant | Lactose 60, Microcrystalline Cellulose 60, Carboxymethyl Starch Sodium 5, Hypromellose 0.6, Magnesium Stearate 0.75 |
| | Solvent | Water 8, 95% Aqueous ethanol solution 11 (17.1%) |
| | Acidifier | Citric Acid Monohydrate 0.86 (molar ratio of it to Zopiclone is 0.80) |
| | Alkalizer | 5% Aqueous NaOH solution 3.3 (the value of fomula 1 is 1.01) |
| | Preparation Technology | Disperse hypromellose into 95% ethanol and add water and citric acid, stir to dissolve, make them and zopiclone into medicated acid liquid, homogeneously mix lactose, microcrystalline cellulose and ⅔ amount of carboxymethyl starch sodium, add aqueous NaOH solution and then homogeneously mix, add the medicated acid liquid and carry out stirring granulation, finish granule after drying wet granules, add magnesium stearate and ⅓ amount of carboxymethyl starch sodium, homogeneously mix and then press. |
| Coating | Materials | Premix of film-coating (Gastric soluble opadry) 5, Water 21 |
| | Preparation Technology | Stir when adding opadry powder in water, and continue to stir for 45 mins after adding to make the coating solution, and carry out film-coating on the tablet core. |

EXAMPLE 60

Prescription and Preparation Method of Risperidone Tablets (1 mg/tablet)

| | | |
|---|---|---|
| Tablet Core | Drug | Risperidone 1 (0.9%, without pretreatment) |
| | Adjuvant | Lactose 50, Microcrystalline Cellulose 60, Croscarmellose Sodium 2, Sodium Dodecyl Sulfate 1.2, Magnesium Stearate 0.6, Colloidal Silicon Dioxide 0.3 |
| | Solvent | 75% Aqueous ethanol solution 25 (21.6%) |
| | Acidifier | Citric Acid Monohydrate 0.17 (molar ratio of it to Risperidone is 0.33) |
| | Alkalizer | Sodium Citrate Dihydrate 0.36 (the value of fomula 1 is 1.51) |
| | Preparation | Mix risperidone and citric acid and add 75% aqueous ethanol |

| | Technology | solution, and then stir to dissolve, stir when adding sodium dodecyl sulfate and dissolve it to make medicated acid liquid, dissolve sodium citrate dihydrate in appropriate water and homogeneously mix it with lactose, microcrystalline cellulose, add the medicated acid liquid and carry out stirring granulation, finish granule after drying wet granules, add magnesium stearate, colloidal silicon dioxide and croscarmellose sodium, homogeneously mix and then press. |
|---|---|---|
| Coating | Materials Preparation Technology | Premix of film-coating (Gastric soluble opadry) 5, Water 21 Stir when adding opadry powder in water, and continue to stir for 45 mins after adding to make the coating solution, and carry out film-coating on the tablet core. |

EXAMPLE 61

Prescription and Preparation Method of Risperidone Capsules (2 mg/tablet)

| | |
|---|---|
| Drug | Risperidone 2 (1.7%, without pretreatment) |
| Adjuvant | Lactose 50, Microcrystalline Cellulose 60, Croscarmellose Sodium 2, Povidone-K30 3, Magnesium Stearate 0.6, Colloidal Silicon Dioxide 0.3 |
| Solvent | Water 15 (17.3%) |
| Acidifier | 10% Aqueous HCl solution 3.7 (molar ratio of it to Risperidone is 2.08) |
| Alkalizer | 20% Aqueous NaOH solution 2.25 (the value of fomula 1 is 1.1) |
| Preparation Technology | Mix risperidone and 10% aqueous HCl solution, add water and stir to dissolve, stir when adding povidone K30 and dissolved to make medicated acid liquid, homogeneously mix 20% aqueous NaOH solution and lactose, microcrystalline cellulose, add the medicated acid liquid and made into soft material, carry out extrusion granulation, finish granule after drying wet granules, add magnesium stearate, colloidal silicon dioxide and croscarmellose sodium, homogeneously mix and then capsule them. |

EXAMPLE 62

Prescription and Preparation Method of Risperidone Tablets (1 mg/tablet)

| | | |
|---|---|---|
| Tablet Core | Drug | Risperidone 1 (0.9%, without pretreatment) |
| | Adjuvant | Mannitol 50, Microcrystalline Cellulose 60, Croscarmellose Sodium 2, Povidone-K30 1, Colloidal Silicon Dioxide 0.2, Sodium octadecyl fumarate 0.8 |
| | Solvent | Water 28 (24.2%) |
| | Acidifier | Citric Acid Monohydrate 0.57 (molar ratio of it to Risperidone is 1.11) |
| | Alkalizer | Sodium Citrate Dihydrate 0.08 (the value of formula 1 is 0.10) |
| | Preparation Technology | Mix risperidone and citric acid monohydrate, adding water, mix and stir to dissolve, stir when adding povidone K30 to dissolve, add 20% amount of mannitol and homogeneously mix to prepare medicated acid liquid, dissolve sodium citrate dihydrate with a little water and homogeneously mix it with the left mannitol, microcrystalline cellulose, add the medicated acid liquid and carry out stirring granulation, finish granule after drying wet granules, add sodium octadecyl fumarate, colloidal silicon dioxide and croscarmellose sodium, homogeneously mix and then press. |
| Coating | Materials Preparation Technology | Premix of film-coating (Gastric soluble opadry) 5, Water 21 Stir when adding opadry powder in water, and continue to stir for 45 mins after adding to make the coating solution, and carry out film-coating on the tablet core. |

EXAMPLE 63

Prescription and Preparation Method of Risperidone Tablets (1 mg/tablet)

| Tablet Core | Drug | Risperidone 1 (0.9%, without pretreatment) |
|---|---|---|
| | Adjuvant | Lactose 50, Microcrystalline Cellulose 60, Croscarmellose Sodium 2, Povidone-K30 3, Colloidal Silicon Dioxide 0.2, Magnesium Stearate 0.8 |
| | Solvent | 75% Aqueous ethanol solution 18 15.6% |
| | Acidifier | 10% Aqueous HCl solution 0.71 (molar ratio of it to Risperidone is 0.80) |
| | Alkalizer | 1% Aqueous NaOH solution 0.1 (the value of fomula 1 is 0.01) |
| | Preparation Technology | Mix risperidone and 10% aqueous HCl solution, add water, then mix and stir to dissolve, stir when adding povidone K30 to dissolve to prepare medicated acid liquid, homogeneously mix 1% aqueous NaOH solution, lactose, and microcrystalline cellulose, add the medicated acid liquid and carry out stirring granulation, finish granule after drying wet granules, add magnesium stearate, colloidal silicon dioxide and croscarmellose sodium, homogeneously mix and then press. |
| Coating | Materials | Premix of film-coating (Gastric soluble opadry) 5, Water 21 |
| | Preparation Technology | Stir when adding opadry powder in water, and continue to stir for 45 mins after adding to make the coating solution, and carry out film-coating on the tablet core. |

EXAMPLE 64

Prescription and Preparation Method of Risperidone Tablets (1 mg/tablet)

| Tablet Core | Drug | Risperidone 1 (0.8%, without pretreatment) |
|---|---|---|
| | Adjuvant | Lactose 80, Starch 30, Carboxymethyl Starch Sodium 6, Povidone-K30 3, Magnesium Stearate 0.7 |
| | Solvent | Water 20 19.8% |
| | Acidifier | Citric Acid Monohydrate 0.36 (molar ratio of it to Risperidone is 0.70) |
| | Alkalizer | 1% Aqueous $Na_2CO_3$ solution 4 (the value of fomula 1 is 0.44) |
| | Preparation Technology | Mix risperidone and citric acid monohydrate, add water, then mix and stir to dissolve, stir when adding povidone K30 to dissolve to make medicated acid liquid, homogeneously mix lactose, starch, 70% amount of carboxymethyl starch sodium and 1% aqueous $Na_2CO_3$ solution, add the medicated acid liquid and carry out stirring granulation, finish granule after drying wet granules, add magnesium stearate and the left 30% amount of carboxymethyl starch sodium, homogeneously mix and then press. |
| Coating | Materials | Premix of film-coating (Gastric soluble opadry) 5, Water 21 |
| | Preparation Technology | Stir when adding opadry powder in water, and continue to stir for 45 mins after adding to make the coating solution, and carry out film-coating on the tablet core. |

EXAMPLE 65

Prescription and Preparation Method of Risperidone Orally Disintegrating Tablets (1 mg/tablet)

| Tablet Core | Drug | Risperidone 1 (0.6%, without pretreatment) |
|---|---|---|
| | Adjuvant | Mannitol 120, Microcrystalline Cellulose 30, Crosslinked Polyvinylpyrrolidone 10, Sodium Dodecyl Sulfate 0.3, Aspartame 0.8, Sodium Octadecyl Fumarate 1.2, Colloidal Silicon Dioxide 0.3 |
| | Solvent | Water 26 17.2% |
| | Acidifier | 10% Aqueous HCl solution 1.06 (molar ratio of it to Risperidone is 1.19) |
| | Alkalizer | 10% Aqueous NaOH solution 1.2 (the value of fomula 1 is 1.03) |
| | Preparation Technology | Disperse risperidone and sodium dodecyl sulfate into water, add 10% aqueous HCl solution and then stir to dissolve to make medicated acid liquid, homogeneously mix mannitol, aspartame, microcrystalline cellulose and 10% aqueous NaOH solution to |

|  |  |  |
|---|---|---|
|  |  | make mixed powder, mix the mixed power and the medicated acid liquid and make them into soft material, carry out extrusion granulation, finish granule after drying wet granules, add colloidal silicon dioxide, sodium octadecyl fumarate and crosslinked polyvinylpyrrolidone, homogeneously mix and then press. |
| Coating | Materials | Premix of film-coating (Gastric soluble opadry) 5, Water 21 |
|  | Preparation Technology | Stir when adding opadry powder in water, and continue to stir for 45 mins after adding to make the coating solution, and carry out film-coating on the tablet core. |

EXAMPLE 66

Prescription and Preparation Method of Risperidone Tablets (2 mg/tablet)

| Tablet Core | Drug | Risperidone 2 (1.6%, without pretreatment) |
|---|---|---|
|  | Adjuvant | Lactose 60, Microcrystalline Cellulose 60, Sodium Dodecyl Sulfate 0.13, Crosslinked Polyvinylpyrrolidone 2, Sodium Octadecyl Fumarate 1, Colloidal Silicon Dioxide 0.2 |
|  | Solvent | 75% Aqueous ethanol solution 20 (20.3%) |
|  | Acidifier | 5% Aqueous HCl solution 3.9 (molar ratio of it to Risperidone is 1.10) |
|  | Alkalizer | 10% Aqueous NaOH solution 2 (the value of fomula 1 is 0.94) |
|  | Preparation Technology | Stir and dissolve risperidone, 75% aqueous ethanol solution, 5% aqueous HCl solution and sodium dodecyl sulfate to make medicated acid liquid, homogeneously mix lactose, microcrystalline cellulose and 10% aqueous NaOH solution, add the medicated acid liquid and carry out stirring granulation, finish granule after drying wet granules, add sodium octadecyl fumarate, colloidal silicon dioxide and crosslinked polyvinylpyrrolidone, homogeneously mix and then press. |
| Coating | Materials | Premix of film-coating (Gastric soluble opadry) 5, Water 21 |
|  | Preparation Technology | Stir when adding opadry powder in water, and continue to stir for 45 mins after adding to make the coating solution, and carry out film-coating on the tablet core. |

EXAMPLE 67

Prescription and Preparation Method of Risperidone Tablets (1 mg/tablet)

| Tablet Core | Drug | Risperidone 1 (1.0%, without pretreatment) |
|---|---|---|
|  | Adjuvant | Mannitol 50, Microcrystalline Cellulose 50, Croscarmellose Sodium 2, Magnesium Stearate 0.9 |
|  | Solvent | Water 20 (20.9%) |
|  | Acidifier | 5% Aqueous HCl solution 1.8 (molar ratio of it to Risperidone is 1.01) |
|  | Alkalizer | 1% Aqueous Glycocoll solution 2 (the value of fomula 1 is 0.11) |
|  | Preparation Technology | Mix and stir risperidone and 5% aqueous HCl solution, add water and then stir to dissolve to make medicated acid liquid, homogeneously mix mannitol, microcrystalline cellulose, 1% aqueous glycocoll solution and croscarmellose sodium, add the above medicated acid liquid, carry out stirring granulation, finish granule after drying wet granules, add magnesium stearate and then press. |
| Coating | Materials | Premix of film-coating (Gastric soluble opadry) 4.7, Water 20 |
|  | Preparation Technology | Stir when adding opadry powder in water, and continue to stir for 45 mins after adding to make the coating solution, and carry out film-coating on the tablet core. |

EXAMPLE 68

Prescription and Preparation Method of Risperidone Tablets (1 mg/tablet)

| Tablet Core | Drug | Risperidone 1 (0.9%, without pretreatment) |
|---|---|---|
| | Adjuvant | Mannitol 50, Microcrystalline Cellulose 60, Croscarmellose Sodium 2, Colloidal Silicon Dioxide 0.2, Sodium Octadecyl Fumarate 0.8 |
| | Solvent | Water 20 (20.2%) |
| | Acidifier | 5% Aqueous HCl solution 2.3 (molar ratio of it to Risperidone is 1.29) |
| | Alkalizer | 10% $Na_2CO_3$ solution 1 (the value of fomula 1 is 0.60) |
| | Preparation Technology | Mix risperidone and 5% aqueous HCl solution, add water and then mix and stir to dissolve, add 20% amount of mannitol and homogeneously mix to make medicated acid liquid, homogeneously mix the left mannitol, microcrystalline cellulose and 10% $Na_2CO_3$ solution, add the medicated acid liquid and carry out stirring granulation, finish granule after drying wet granules, add sodium octadecyl fumarate, colloidal silicon dioxide and croscarmellose sodium, homogeneously mix and then press. |
| Coating | Materials | Premix of film-coating (Gastric soluble opadry) 5, Water 21 |
| | Preparation Technology | Stir when adding opadry powder in water, and continue to stir for 45 mins after adding to make the coating solution, and carry out film-coating on the tablet core. |

EXAMPLE 69

Prescription and Preparation Method of Risperidone Tablets (1 mg/tablet)

| Tablet Core | Drug | Risperidone 1 (0.9%, without pretreatment) |
|---|---|---|
| | Adjuvant | Mannitol 50, Microcrystalline Cellulose 60, Croscarmellose Sodium 2, Povidone-K30 1.5, Colloidal Silicon Dioxide 0.3, Magnesium Stearate 0.6 |
| | Solvent | Water 18 (21.0%) |
| | Acidifier | 5% Aqueous HCl solution 2.6 (molar ratio of it to Risperidone is 1.46) |
| | Alkalizer | 5% Sodium Citrate Dihydrate solution 4 (the value of fomula 1 is 0.19) |
| | Preparation Technology | Mix risperidone and 5% aqueous HCl solution, add water and then mix and stir to dissolve, stir when adding povidone K30 to dissolve, homogeneously stir to make medicated acid liquid, homogeneously mix mannitol, microcrystalline cellulose and 5% sodium citrate dihydrate solution, add the medicated acid liquid and carry out stirring granulation, finish granule after drying wet granules, add magnesium stearate, colloidal silicon dioxide and croscarmellose sodium, homogeneously mix and then press. |
| Coating | Materials | Premix of film-coating (Gastric soluble opadry) 5, Water 21 |
| | Preparation Technology | Stir when adding opadry powder in water, and continue to stir for 45 mins after adding to make the coating solution, and carry out film-coating on the tablet core. |

EXAMPLE 70

Prescription and Preparation Method of Risperidone Tablets (1 mg/tablet)

| Tablet Core | Drug | Risperidone 1 (0.9%, without pretreatment) |
|---|---|---|
| | Adjuvant | Lactose 50, Microcrystalline Cellulose 60, Croscarmellose Sodium 2, Povidone K30 3, Magnesium Stearate 0.6, Colloidal Silicon Dioxide 0.3 |
| | Solvent | 75% Aqueous ethanol solution 25 (21.3%) |
| | Acidifier | Citric Acid Monohydrate 0.17 (molar ratio of it to Risperidone is 0.33) |
| | Alkalizer | Sodium Citrate Dihydrate 0.23 (the value of fomula 1 is 0.97) |

|  |  |  |
| --- | --- | --- |
|  | Preparation Technology | Mix risperidone and citric acid, add 75% aqueous ethanol solution and then mix and stir to dissolve, stir when adding povidone K30 to dissolve to make medicated acid liquid, homogeneously mix lactose, microcrystalline cellulose and sodium citrate, add the medicated acid liquid and carry out stirring granulation, finish granule after drying wet granules, add magnesium stearate, colloidal silicon dioxide and croscarmellose sodium, homogeneously mix and then press. |
| Coating | Materials | Premix of film-coating (Gastric soluble opadry) 5, Water 21 |
|  | Preparation Technology | Stir when adding opadry powder in water, and continue to stir for 45 mins after adding to make the coating solution, and carry out film-coating on the tablet core. |

EXAMPLE 71

Prescription and Preparation Method of Risperidone Tablets (2 mg/tablet)

|  |  |  |
| --- | --- | --- |
| Tablet Core | Drug | Risperidone 2 (1.7%, without pretreatment) |
|  | Adjuvant | Mannitol 50, Microcrystalline Cellulose 60, Crosslinked Polyvinylpyrrolidone 2, Povidone K30 3, Magnesium Stearate 0.6, Colloidal Silicon Dioxide 0.3 |
|  | Solvent | 75% Aqueous ethanol solution 25 (21.1%) |
|  | Acidifier | DL-Tartaric Acid 0.2 (mole ratio of it to Risperidone is 0.27) |
|  | Alkalizer | DL-Sodium Tartrate Dihydrate 0.31 (the value of fomula 1 is 1.01) |
|  | Preparation Technology | Mix risperidone and DL-tartaric acid, add 75% aqueous ethanol solution and then mix and stir to dissolve, stir when adding povidone K30 to dissolve to make medicated acid liquid, homogeneously mix mannitol, microcrystalline cellulose and DL-sodium tartrate, add the medicated acid liquid and carry out stirring granulation, finish granule after drying wet granules, add magnesium stearate, colloidal silicon dioxide and crosslinked polyvinylpyrrolidone, homogeneously mix and then press. |
| Coating | Materials | Premix of film-coating (gastric soluble opadry) 5, Water 21 |
|  | Preparation Technology | Stir when adding opadry powder in water, and continue to stir for 45 mins after adding to make the coating solution, and carry out film-coating on the tablet core. |

EXAMPLE 72

Prescription and Preparation Method of Dipyridamole Tablets (25 mg/tablet)

|  |  |
| --- | --- |
| Drug | Dipyridamole 25 (11.6%, without pretreatment) |
| Adjuvant | Mannitol 80, Microcrystalline Cellulose 120, Carboxymethyl Starch Sodium 5, Povidone K30 3, Magnesium Stearate 1.5, Talcum Powder 3 |
| Solvent | 95% Aqueous ethanol solution 35(23.2%) |
| Acidifier | 10% Aqueous HCl solution 15 (molar ratio of it to Dipyridamole is 0.83) |
| Alkalizer | Glycocoll 3 (the value of fomula 1 is 0.97) |
| Preparation Technology | Mix dipyridamole, 95% aqueous ethanol solution, and 10% aqueous HCl solution and stir to dissolve, stir when adding povidone K30 to dissolve to make medicated acid liquid, homogeneously mix mannitol, microcrystalline cellulose and glycocoll, add the medicated acid liquid and carry out granulation, after finishing granule, add carboxymethyl starch sodium, magnesium stearate and talcum powder, homogeneously mix and then press. |

EXAMPLE 73

Prescription and Preparation Method of Dipyridamole Tablets (25 mg/tablet)

| | |
|---|---|
| Drug | Dipyridamole 25 (14.9%, without pretreatment) |
| Adjuvant | Lactose 60, Microcrystalline Cellulose 100, Crosslinked Polyvinylpyrrolidone 3, Povidone K30 2, Magnesium Stearate 0.9 |
| Solvent | 75% Aqueous ethanol solution 50 (62.5%) |
| Acidifier | 5% Aqueous HCl solution 38 (molar ratio of it to Dipyridamole is 1.05) |
| Alkalizer | 10% Aqueous NaOH solution 19 (the value of fomula 1 is 0.91) |
| Preparation Technology | Mix dipyridamole and povidone K30, add 5% aqueous HCl solution and stir to mix, add 75% ethanol and then stir to dissolve, stir when adding 10% aqueous NaOH solution to form granulating liquid, add lactose, microcrystalline cellulose into fluidized spray granulator, carry out fluidized spray granulation after finishing granule, add crosslinked polyvinylpyrrolidone, magnesium stearate and then press. |

EXAMPLE 74

Prescription and Preparation Method of Aripiprazole Tablets (5 mg/tablet)

| | |
|---|---|
| Drug | Aripiprazole 5 (4.3%) (without pretreatment) |
| Adjuvant | Lactose 75, Microcrystalline Cellulose 30, Polyethyleneglycol 6, Magnesium Stearate 0.6 |
| Solvent | 95% Aqueous ethanol solution 20 (23.8%) |
| Acidifier | 10% Aqueous HCl solution 4.05 (molar ratio of it to Aripiprazole is 1.0) |
| Alkalizer | 10% Aqueous NaOH solution 4.44 (the value of fomula 1 is 1.0) |
| Preparation Technology | Dispers aripiprazole into 95% aqueous ethanol solution, add 10% aqueous HCl solution and polyethyleneglycol, stir to dissolve to make medicated acid liquid, add 1/5 amount of lactose, stir when adding 10% aqueous NaOH solution, carry out stirring granulation with 4/5 amount of microcrystalline cellulose, finish granule after drying wet granules, add magnesium stearate, homogeneously mix and then press. |

EXAMPLE 75

Prescription and Preparation Method of Aripiprazole Tablets (5 mg/tablet)

| | |
|---|---|
| Drug | Aripiprazole 5 (4.2%) (without pretreatment) |
| Adjuvant | Lactose 60, Microcrystalline Cellulose 30, Hydroxypropyl-β-Cyclodextrin 15, Povidone (K30) 2, Crosslinked Polyvinylpyrrolidone 2, Magnesium Stearate 0.6 |
| Solvent | 85% Aqueous ethanol solution 24 (20.0%) |
| Acidifier | Citric Acid Monohydrate 2.35 (molar ratio of it to Aripiprazole is 1.0) |
| Alkalizer | Sodium Citrate Dihydrate 3.28 (the value of fomula 1 is 1.0) |
| Preparation Technology | Disperse aripiprazole into 85% aqueous ethanol solution, add citric acid and stir to dissolve, add hydroxypropyl-β-cyclodextrin and povidone to make medicated acid liquid, stir when adding sodium citrate mixed powder (homogeneously mixing sodium citratea and 1/7 amount of lactose beforehand), carry out stirring granulation with the left lactose and microcrystalline cellulose, finish granule after drying wet granules, add magnesium stearate and crosslinked polyvinylpyrrolidone, homogeneously mix and then press. |

EXAMPLE 76

Prescription and Preparation Method of Aripiprazole Tablets (5 mg/tablet)

| | |
|---|---|
| Drug | Aripiprazole 5 (4.2%) (without pretreatment) |
| Adjuvant | Lactose 75, Microcrystalline Cellulose 30, Povidone (K30) 6, Carboxymethyl Starch Sodium 2, Magnesium Stearate 0.6 |
| Solvent | 95% Aqueous ethanol solution 20 (24.2%) |
| Acidifier | 10% Aqueous HCl solution 4.05 (molar ratio of it to Aripiprazole is 1.0) |
| Alkalizer | $Na_2CO_3$ 0.59 (the value of fomula 1 is 1.0) |
| Preparation Technology | Disperse aripiprazole into 95% ethanol, add 10% aqueous HCl solution and povidone to make medicated acid liquid, add ⅕ amount of lactose, stir when adding $Na_2CO_3$ solution (10% water solution), and carry out stirring granulation with ⅘ amount of lactose and microcrystalline cellulose, finish granule after drying wet granules, add magnesium stearate and carboxymethyl starch sodium, homogeneously mix and then press. |

EXAMPLE 77

Prescription and Preparation Method of Aripiprazole Granules

| | |
|---|---|
| Drug | Aripiprazole 5 (4.1%) (without pretreatment) |
| Adjuvant | Lactose 100, Sucrose 10 |
| Solvent | 85% Aqueous ethanol solution 13 (10.8%) |
| Acidifier | Citric Acid Monohydrate 2.35 (molar ratio of it to Aripiprazole is 1.0) |
| Alkalizer | Sodium Citrate Dihydrate 3.28 (the value of fomula 1 is 1.0) |
| Preparation Technology | Disperse aripiprazole into 85% aqueous ethanol solution, add citric acid and stir to dissolve to make medicated acid liquid, stir when adding sodium citrate mixed powder (homogeneously mixing sodium citrate and ⅐ amount of lactose beforehand), and then carry out stirring granulation with the left lactose and sucrose, finish granule after drying wet granules. |

EXAMPLE 78

Prescription and Preparation Method of Aripiprazole Granules

| | |
|---|---|
| Drug | Aripiprazole 5 (1.8%) (without pretreatment) |
| Adjuvant | Lactose 250, Hydroxypropyl-β-Cyclodextrin 20, Povidone (K30) 2, Tween-80 0.3 |
| Solvent | 95% Aqueous ethanol solution 15.5 (8.3%) |
| Acidifier | 10% Aqueous HCl solution 4.05 (molar ratio of it to Aripiprazole is 1.0) |
| Alkalizer | 10% Aqueous NaOH solution 4.44 (the value of fomula 1 is 1.0) |
| Preparation Technology | Stir and dissolve aripiprazole, 95% ethanol, 10% aqueous HCl solution, povidone and hydroxypropyl-β-cyclodextrin, add tween-80 to make medicated acid liquid, homogeneously mix lactose and 10% aqueous NaOH solution, add the medicated acid liquid and carry out stirring granulation, finish granule after drying wet granules. |

EXAMPLE 79

Prescription and Preparation Method of Eszopiclone Tablets (2 mg/tablet)

| | | |
|---|---|---|
| Tablet Core | Drug | Eszopiclone 2 (2.7%, without pretreatment) |
| | Adjuvant | Lactose 40, Microcrystalline Cellulose 25, Povidone K30 1, Hydroxypropyl-β-Cyclodextrin 4, Crosslinked Polyvinylpyrrolidone 1, Colloidal Silicon Dioxide 0.2, Magnesium Stearate 0.3 |
| | Solvent | Water 13 (23.1%) |
| | Acidifier | 10% Aqueous HCl solution 1.9 (molar ratio of it to Eszopiclone is 1.01) |

-continued

| | Alkalizer | Na$_2$CO$_3$ 0.28 (the value of fomula 1 is 1.01) |
| --- | --- | --- |
| | Preparation Technology | Stir and dissolve eszopiclone, water and 10% aqueous HCl solution, add hydroxypropyl-β-cyclodextrin and povidone to make medicated acid liquid, stir when adding mixed powder of Na$_2$CO$_3$ and lactose (homogeneously mixing Na$_2$CO$_3$ and 1/10 amount of lactose beforehand), add them into the left lactose and microcrystalline cellulose and carry out stirring granulation, finish granule after drying wet granules, add magnesium stearate, crosslinked polyvinylpyrrolidone and colloidal silicon dioxide, homogeneously mix and then press. |
| Coating | Materials | Premix of film-coating (Gastric soluble opadry) 3, Water 13 |
| | Preparation Technology | Stir when adding opadry powder in water, and continue to stir for 45 mins after adding to make the coating solution, and carry out film-coating on the tablet core. |

EXAMPLE 80

Prescription and Preparation Method of Eszopiclone Tablets (2 mg/tablet)

| Tablet Core | Drug | Eszopiclone 2 (2.6%, without pretreatment) |
| --- | --- | --- |
| | Adjuvant | Lactose 50, Microcrystalline Cellulose 20, Hydroxypropyl-β-Cyclodextrin 2, Carboxymethyl Starch Sodium 1, Magnesium Stearate 0.3, Colloidal Silicon Dioxide 0.1 |
| | Solvent | Water 12 (20.6%) |
| | Acidifier | 10% Aqueous HCl solution 1.9 (molar ratio of it to Eszopiclone is 1.01) |
| | Alkalizer | 10% Aqueous NaOH solution 2.1 (the value of fomula 1 is 1.01) |
| | Preparation Technology Method | Stir and dissolve eszopiclone, water and 10% aqueous HCl solution, add hydroxypropyl-β-cyclodextrin to make medicated acid liquid, add 1/3 amount of lactose, stir when adding 10% aqueous NaOH solution and homogeneously mix, add them into the left lactose and microcrystalline cellulose and carry out stirring granulation, finish granule after drying wet granules, add magnesium stearate, carboxymethyl starch sodium and colloidal silicon dioxide, homogeneously mix and then press. |
| Coating | Materials | Premix of film-coating (Gastric soluble opadry) 2.5, Water 11 |
| | Preparation Technology | Stir when adding opadry powder in water, and continue to stir for 45 mins after adding to make the coating solution, and carry out film-coating on the tablet core. |

EXAMPLE 81

Prescription and Preparation Method of Eszopiclone Tablets (2 mg/tablet)

| Tablet Core | Drug | Eszopiclone 2 (2.5%, without pretreatment) |
| --- | --- | --- |
| | Adjuvant | Lactose 50, Microcrystalline Cellulose 20, Polyethyleneglycol (6000) 2, Carboxymethyl Starch Sodium 3.6, Colloidal Silicon Dioxide 0.1, Magnesium Stearate 0.3 |
| | Solvent | Water 16 (19.6%) |
| | Acidifier | Citric Acid Monohydrate 1.08 (molar ratio of it to Eszopiclone is 1.0) |
| | Alkalizer | Sodium Citrate Dihydrate 1.51 (the value of fomula 1 is 1.0) |
| | Preparation Technology | Stir and dissolve eszopiclone, 3/4 amount of water and citric acid, add polyethyleneglycol to make medicated acid liquid, add 1/3 amount of lactose, stir when adding sodium citrate solution (dissolving sodium citrate in 1/4 amount of water), add them into microcrystalline cellulose, 2/3 amount of carboxymethyl starch sodium and the left lactose, carry out stirring granulation, finish granule after drying wet granules, homogeneously mix with magnesium stearate, colloidal silicon dioxide and 1/3 amount of carboxymethyl starch sodium and then press. |

-continued

| Coating | Materials Preparation Technology | Premix of film-coating (Gastric soluble opadry) 2.5, Water 11 Stir when adding opadry powder in water, and continue to stir for 45 mins after adding to make the coating solution, and carry out film-coating on the tablet core. |

EXAMPLE 82

Prescription and Preparation Method of Eszopiclone Capsules (2 mg/tablet)

Make granules before pressing in Example 80 pass through 30 mesh sieve and then homogeneously mix, and capsule them.

| Tablet Core | Drug | Zopiclone 3.75 (3.4%, without pretreatment) |
|---|---|---|
| | Adjuvant | Lactose 70, Microcrystalline Cellulose 30, Povidone K30 1.5, Hydroxypropyl-β-Cyclodextrin 3.75, Crosslinked Polyvinylpyrrolidone 1, Colloidal Silicon Dioxide 0.2, Magnesium Stearate 0.8 |
| | Solvent | Water 18 (18.6%) |
| | Acidifier | 10% Aqueous HCl solution 3.1 (molar ratio of it to Zopiclone is 0.88) |
| | Alkalizer | $Na_2CO_3$ 0.45 (the value of fomula 1 is 1.0) |
| | Preparation Technology | Mix and dissolve zopiclone, 10% aqueous HCl solution and water, add hydroxypropyl-β-cyclodextrin, povidone K30, homogeneously mix them to make medicated acid liquid, stir when adding mixed powder of $Na_2CO_3$ and lactose (homogeneously mixing $Na_2CO_3$ and 1/10 amount of lactose beforehand), add them into the left lactose and microcrystalline cellulose and carry out stirring granulation, finish granule after drying wet granules, add magnesium stearate, crosslinked polyvinylpyrrolidone and colloidal silicon dioxide, homogeneously mix and then press. |
| Coating | Materials Preparation Technology | Premix of film-coating (Gastric soluble opadry) 3.5, Water 15 Stir when adding opadry powder in water, and continue to stir for 45 mins after adding to make the coating solution, and carry out film-coating on the tablet core. |

EXAMPLE 84

Prescription and Preparation Method of Zopiclone Tablets (3.75 mg/tablet)

| Tablet Core | Drug | Zopiclone 3.75 (3.4%, without pretreatment) |
|---|---|---|
| | Adjuvant | Lactose 70, Microcrystalline Cellulose 25, Polyethyleneglycol(6000) 2, Hydroxypropyl-β-Cyclodextrin 5, Carboxymethyl Starch Sodium 4, Colloidal Silicon Dioxide 0.1, Magnesium Stearate 0.8 |
| | Solvent | Water 21 (19.0%) |
| | Acidifier | Citric Acid Monohydrate 2.03 (molar ratio of it to Zopiclone is 1.0) |
| | Alkalizer | Sodium Citrate Dihydrate 2.84 (the value of fomula 1 is 1.0) |
| | Preparation Technology | Stir and dissolve zopiclone, 2/3 amount of water and citric acid, add polyethyleneglycol and hydroxypropyl-β-cyclodextrin to make medicated acid liquid, add 1/3 amount of lactose, stir when adding sodium citrate solution (dissolving sodium citrate in 1/3 amount of water), add them into microcrystalline cellulose, 2/3 amount of carboxymethyl starch sodium and the left lactose, carry out stirring granulation, finish granule after drying wet granules, homogeneously mix them with magnesium stearate, colloidal silicon dioxide and 1/3 amount of carboxymethyl starch sodium and then press. |
| Coating | Materials Preparation Technology | Premix of film-coating (Gastric soluble opadry) 3.5, Water 15 Stir when adding opadry powder in water, and continue to stir for 45 mins after adding to make the coating solution, and carry out film-coating on the tablet core. |

EXAMPLE 83

Prescription and Preparation Method of Zopiclone Tablets (3.75 mg/tablet)

CONTRASTIVE EXAMPLE 9 AND EXAMPLE 85

Prescription and Preparation Method of Iloperidone Granules

|  | Contrastive Example 9 | Example 85 |
| --- | --- | --- |
| Drug | Iloperidone 2 (sieved by 80 mesh sieve, 1.9%,) | Iloperidone 2 (1.8%, without pretreatment) |
| Adjuvant | Lactose 100, Povidone K30 5 | Lactose 100, Povidone K30 5 |
| Solvent | Water 8(7.5%) | Water 1(7.4%) |
| Acidifier | \ | 20% Glacial Acetic Acid 3.525 (molar ratio of it to Iloperidone is 2.5) |
| Alkalizer | \ | 10% Aqueous NaOH solution 4.7 (the value of formula 1 is 1.0) |
| Preparation Technology | Homogeneously mix iloperidone, lactose and povidone by equivalent increment method, add water, mix and carry out stirring granulation, finish granule after drying wet granules. | Dissolve iloperidone in glacial acetic acid, add povidone K30 and homogeneously mix to make medicated acid liquid; separately, homogeneously mix 10% aqueous NaOH solution and lactose, add the medicated acid liquid and carry out stirring granulation, finish granule after drying wet granules. |

CONTRASTIVE EXAMPLE 10

Prescription and Preparation Method of Iloperidone Tablets (2 mg/tablet)

| | |
| --- | --- |
| Drug | Iloperidone 2 (sieved by 80 mesh sieve, 1.6%,) |
| Adjuvant | Lactose 100, Microcrystalline Cellulose 15, Crosslinked Polyvinylpyrrolidone 4, Povidone K30 5, Magnesium Stearate 0.8 |
| Solvent | Water 17 (13.4%) |
| Preparation Technology | Homogeneously mix iloperidone, lactose, ⅗ amount of povidone, ½ amount of crosslinked polyvinylpyrrolidone and microcrystalline cellulose by equivalent increment method, add aqueous ⅖ amount of povidone solution and carry out stirring granulation, finish granule after drying wet granules, add magnesium stearate and ½ amount of crosslinked polyvinylpyrrolidone, homogeneously mix and then press. |

EXAMPLE 86

Prescription and Preparation Method of Iloperidone Tablets (2 mg/tablet)

| | |
| --- | --- |
| Drug | Iloperidone 2 (1.5%, without pretreatment) |
| Adjuvant | Lactose 100, Microcrystalline Cellulose 15, Hydroxypropyl-β-Cyclodextrin 5, Povidone K30 1.5, Crosslinked Polyvinylpyrrolidone 4, Magnesium Stearate 0.8 |
| Solvent | 50% Aqueous ethanol solution 4 (11.3%) |
| Acidifier | 10% Aqueous Glacial Acetic Acid solution 7.05 (molar ratio of it to Iloperidone is 2.5) |
| Alkalizer | 10% Aqueous NaOH solution 4.7 (the value of fomula 1 is 1.0) |
| Preparation Technology | Dissolve iloperidone in aqueous glacial acetic acid solution and 50% aqueous ethanol solution, add hydroxypropyl-β-cyclodextrin and povidone and homogeneously mix to make medicated acid liquid, add 10 g lactose, stir when adding 10% aqueous NaOH solution and homogeneously mix, add them into the mixture of the left lactose, ½ amount of crosslinked polyvinylpyrrolidone and microcrystalline cellulose, carry out stirring granulation, finish granule after drying wet granules, add ½ amount of crosslinked polyvinylpyrrolidone and magnesium stearate, homogeneously mix and then press. |

EXAMPLE 87

Prescription and Preparation Method of Iloperidone Tablets (2 mg/tablet)

| | |
|---|---|
| Drug | Iloperidone 2 (1.6%, without pretreatment) |
| Adjuvant | Lactose 100, Microcrystalline Cellulose 15, Povidone K30 5, Crosslinked Polyvinylpyrrolidone 4, Magnesium Stearate 0.8 |
| Solvent | Water 3 (11.2%) |
| Acidifier | 10% Glacial Acetic Acid 7.53 (molar ratio of it to Iloperidone is 2.67) |
| Alkalizer | 10% Aqueous NaOH solution 5.02 (the value of fomula 1 is 1.0) |
| Preparation Technology | Dissolve iloperidone with glacial acetic acid and water, add povidone K30 and homogeneously mix to make medicated acid liquid; separately, homogeneously mix 10% aqueous NaOH solution, lactose, ½ amount of crosslinked polyvinylpyrrolidone and microcrystalline cellulose, add the medicated acid liquid and carry out stirring granulation, finish granule after drying wet granules, add ½ amount of crosslinked polyvinylpyrrolidone and magnesium stearate, homogeneously mix and then press. |

EXAMPLE 88

Prescription and Preparation Method of Iloperidone Tablets (2 mg/tablet)

| | |
|---|---|
| Drug | Iloperidone 2 (1.4%, without pretreatment) |
| Adjuvant | Lactose 100, Microcrystalline Cellulose 30, Povidone K30 5, Carboxymethyl Starch Sodium 2, Magnesium Stearate 1 |
| Solvent | Ethanol 12 (12.8%) |
| Acidifier | 10% Glacial Acetic Acid 4.0 (molar ratio of it to Iloperidone is 1.42) |
| Alkalizer | 10% Aqueous NaOH solution 2.64 (the value of fomula 1 is 0.99) |
| Preparation Technology | Dissolve iloperidone, ethanol and glacial acetic acid with the water bath heating at 50° C., add povidone K30 and homogeneously mix to make medicated acid liquid, add ⅓ amount of lactose, stir when adding 10% aqueous NaOH solution and homogeneously mix, add them into the mixture of the left lactose and microcrystalline cellulose and carry out stirring granulation, finish granule after drying wet granules, add carboxymethyl starch sodium and magnesium stearate, homogeneously mix and then press. |

EXAMPLE 89

Prescription and Preparation Method of Iloperidone Tablets (12 mg/tablet)

| | |
|---|---|
| Drug | Iloperidone 12 (5.4%, without pretreatment) |
| Adjuvant | Lactose 120, Microcrystalline Cellulose 50, Starch 20, Polyethyleneglycol-6000 10, Poloxamer 2, Crosslinked Polyvinylpyrrolidone 4, Magnesium Stearate 1.5, Colloidal Silicon Dioxide 0.4 |
| Solvent | Water 80 (53.8%) |
| Acidifier | 10% Glacial Acetic Acid 27.0 (molar ratio of it to Iloperidone is 1.6) |
| Alkalizer | 10% Aqueous NaOH solution 18.2 (the value of fomula 1 is 1.01) |
| Preparation Technology | Dissolve iloperidone, water, poloxamer and glacial acetic acidby 50° C. water bath heating, add polyethyleneglycol and ¹/₁₀ amount of lactose and homogeneously mix, stir when adding 10% aqueous NaOH solution, homogeneously mix to make granulating liquid. Add the left lactose, starch and microcrystalline cellulose into fluidized spray granulator, carry out fluidized spray granulation, add granules into crosslinked polyvinylpyrrolidone, magnesium stearate and colloidal silicon dioxide and then finish granule, homogeneously mix and then press. |

EXAMPLE 90

Prescription and Preparation Method of Agomelatine Tablets (25 mg/tablet)

| | | |
|---|---|---|
| Tablet Core | Drug | Agomelatine 25 (14.9%, without pretreatment) |
| | Adjuvant | Lactose 80, Starch 40, Povidone K30 10, Carboxymethyl Starch Sodium 4, Magnesium Stearate 1 |
| | Solvent | Ethanol 130 (96.2%) |
| | Acidifier | 20% Aqueous HCl solution 18.8 (molar ratio of it to Agomelatine is 1.0) |
| | Alkalizer | 20% Aqueous NaOH solution 20.6 (the value of fomula 1 is 1.0) |
| | Preparation Technology | Mix and dissolve agomelatine, ethanol and 20% HCl, add povidone to make medicated acid liquid, stir when adding 20% aqueous NaOH solution to form granulating liquid, add lactose and starch into fluidized spray granulator, carry out fluidized spray granulation after finishing granule, add carboxymethyl starch sodium and magnesium stearate and then press. |
| Lagging Cover | Materials | Premix of film-coating (Gastric soluble opadry) 7, Water 29 |
| | Preparation Technology | Stir when adding opadry powder in water, and continue to stir for 45 mins after adding to make the coating solution, and carry out film-coating on the tablet core. |

EXAMPLE 91

Prescription and Preparation Method of Eszopiclone Tablets (2 mg/tablet)

| | | |
|---|---|---|
| Tablet Core | Drug | Eszopiclone 2 (2.1%, without pretreatment) |
| | Adjuvant | Lactose 60, Microcrystalline Cellulose 25, Carboxymethyl Starch Sodium 5, Colloidal Silicon Dioxide 0.1, Magnesium Stearate 0.5 |
| | Solvent | Water 16 (17.0%) |
| | Acidifier | Citric Acid Monohydrate 1.1 (molar ratio of it to Eszopiclone is 1.02) |
| | Alkalizer | NaOH 0.523 (the value of fomula 1 is 2.5) |
| | Preparation Technology | Stir and dissolve eszopiclone, ¾ amount of water and citric acid to make medicated acid liquid, add ⅓ amount of lactose, stir when adding aqueous NaOH solution (dissolving NaOH in ¼ amount of water), add them into microcrystalline cellulose, ½ amount of carboxymethyl starch sodium and the left lactose, carry out stirring granulation, finish granule after drying wet granules, homogeneously mix them with magnesium stearate, colloidal silicon dioxide and ½ amount of carboxymethyl starch sodium and then press. |
| Coating | Materials | Premix of film-coating (Gastric soluble opadry) 3.5, Water 15 |
| | Preparation Technology | Stir when adding opadry powder in water, and continue to stir for 45 mins after adding to make the coating solution, and carry out film-coating on the tablet core. |

EFFECT EXAMPLE 1

Comparison Experiments on Particle Size

Test instrument: BT-9300S laser particle size distribution device; BT-800 automatic loop sampling system.

Test condition: the medium of the loop sampling system is water, the volume is about 570 ml and the rotating speed of centrifugal pump is 1600 rpm.

Test method: Add 2 g granules into the loop sampling system and make the absorbance of the system come up to 15%, turn on the ultrasonic dispersion for 3 mins, continuous sample for 6 times, and gain the average particle size. D10, D50 and D90 are corresponding particle sizes when the percentages of cumulative particle size distribution are up to 10%, 50% and 90% respectively.

1) Comparison on the Particle Sizes of Aripiprazole

Test purpose: compare the particle sizes of aripiprazole in the aripiprazole granules of the contrastive examples 1~2, examples 1~2 and 77~78.

| | particle size (µm) | | | |
|---|---|---|---|---|
| Example | Average particle size (volume) | $D_{10}$ | $D_{50}$ | $D_{90}$ |
| Contrastive 1 | 89.51 | 13.21 | 77.12 | 184.46 |
| Contrastive 2 | 21.47 | 1.41 | 16.59 | 49.36 |
| 1 | 12.09 | 1.22 | 9.65 | 25.25 |
| 2 | 5.28 | 0.86 | 3.66 | 12.23 |
| 77 | 8.12 | 1.35 | 5.20 | 17.20 |
| 78 | 2.80 | 0.55 | 1.90 | 5.44 |

It can be seen from the above comparison that, particle sizes of aripiprazole granules obtained from Examples 1, 2, 77 and 78 in this invention is smaller than that from Contrastive Examples 1 and 2, and it is beneficial to the dissolution of active pharmaceutical ingredients.

2) Comparison on the Particle Sizes of Iloperidone

Test purpose: compare the particle sizes of iloperidone in the iloperidone granules of Contrastive Example 9 and Example 85.

| Example | particle size (μm) | | | |
|---|---|---|---|---|
| | Average particle size (volume) | $D_{10}$ | $D_{50}$ | $D_{90}$ |
| Contrastive 9 | 51.78 | 11.4 | 36.96 | 89.11 |
| 85 | 10.86 | 0.76 | 4.36 | 32.74 |

EFFECT EXAMPLE 2

Comparison Experiments on Dissolution (1) Comparison on Dissolution of Aripiprazole Tablets in Contrastive Examples 3 and 4, Examples 3~5, and Example 75.

Method of Dissolution Experiment: following dissolution mensuration (Chinese Pharmacopoeia 2005 Volume 2 appendix X C No. 2), take sample and make 500 ml pH 4.0 acetate buffer solution (0.05 mol/L acetic acid –0.05 mol/L sodium acetate=16.4:3.6) as solvent, rotation rate is 50 rpm, carry on according to the mensuration, take 5 ml solution at the 5th, 10th, 20th, 30th, 45th min respectively, replenish 5 ml dissolution medium to each dissolution cup, filter the samples, take subsequent filtrate as sample solution, and prepare the reference solution. Detection is respectively followed by high performance liquid chromatography (Chinese Pharmacopoeia 2005 Volume 2 appendix V D), and use octadecylsilane chemically bonded silica as filler; and use methyl alcohol –0.1% triethylamine solution (90:10) as mobile phase; detection at 255 nm, and calculate the dissolution of each tablet.

| Example | Dissolution (%) | | | | |
|---|---|---|---|---|---|
| | 5 min | 10 min | 20 min | 30 min | 45 min |
| Contrastive 3 | 25.6 | 56.1 | 84.1 | 94.4 | 97.3 |
| 3 | 34.5 | 67.3 | 90.7 | 95.2 | 98.5 |
| 4 | 35.1 | 66.4 | 91.0 | 96.9 | 99.7 |
| 75 | 48.2 | 75.6 | 93.4 | 99.5 | 99.4 |
| Contrastive 4 | 27.7 | 35.0 | 40.5 | 45.0 | 50.4 |
| 5 | 46.7 | 60.2 | 78.0 | 86.0 | 93.7 |

(2) Comparison on the Eszopiclone Preparations' Dissolution in Contrastive Example 5, Examples 6~11, and Example 79

Method of Dissolution Experiment: following dissolution mensuration (Chinese Pharmacopoeia 2005 Volume 2 appendix X C No. 3), take samples and make 200 ml water as solvent, rotation rate is 50 rpm, carry on according to the mensuration, and prepare reference solution. According to ultraviolet-visible spectrophotometry (Chinese Pharmacopoeia 2005 Volume 2 appendix IV A), detect absorbance at 304 nm respectively, and calculate the dissolution of each tablet.

| Example | Dissolution (%) | | | |
|---|---|---|---|---|
| | 10 min | 20 min | 30 min | 40 min |
| Contrastive 5 | 35.2 | 61.4 | 88.9 | 92.3 |
| 6 | 53.5 | 89.7 | 95.2 | 99.5 |
| 7 | 67.3 | 92.5 | 99.8 | 100.5 |
| 8 | 60.7 | 90.6 | 98.3 | 100.1 |
| 9 | 62.1 | 95.5 | 99.2 | 99.7 |
| 10 | 65.8 | 93.9 | 98.0 | 99.2 |
| 11 | 58.9 | 92.9 | 98.4 | 99.9 |
| 79 | 70.4 | 97.3 | 99.6 | 99.8 |

(3) Comparison on the Dissolution of Zopiclone Tablets of Contrastive Example 6, Examples 12~17 and Example 84

Method of Dissolution Experiment: following dissolution mensuration (Chinese Pharmacopoeia 2005 Volume 2 appendix X C No. 3), take samples and make 200 ml water as solvent, rotation rate is 50 rpm, carry on according to the mensuration, and prepare reference solution. According to ultraviolet-visible spectrophotometry (Chinese Pharmacopoeia 2005 Volume 2 appendix IV A), detect absorbance at 304 nm respectively, and calculate the dissolution of each tablet.

| Example | Dissolution (%) | | | |
|---|---|---|---|---|
| | 10 min | 20 min | 30 min | 40 min |
| Contrastive 6 | 40.1 | 64.6 | 89.3 | 94.9 |
| 12 | 60.6 | 91.4 | 98.5 | 99.7 |
| 13 | 64.0 | 90.2 | 100.2 | 100.6 |
| 14 | 71.3 | 93.1 | 100.6 | 100.5 |
| 15 | 70.9 | 93.6 | 99.8 | 99.6 |
| 16 | 64.7 | 90.2 | 100.3 | 100.1 |
| 17 | 73.6 | 94.1 | 99.8 | 99.7 |
| 84 | 75.2 | 95.4 | 99.7 | 99.8 |

(4) Comparison on Dissolution of Risperidone Tablets of Contrastive Example 7 and Examples 18~20

Method of Dissolution Experiment: following dissolution mensuration (Chinese Pharmacopoeia 2005 Volume 2 appendix X C No. 2), take samples and make 200 ml water as solvent, rotation rate is 50 rpm, carry on according to the mensuration, take 5 ml solution at the 15th, 30th, 45th min respectively, replenish each 5 ml dissolution medium, filter the samples and discard filtrate of the prefiltration, take subsequent filtrate as sample solution, and prepare reference solution. Detection is respectively followed by high performance liquid chromatography (Chinese Pharmacopoeia 2005 Volume 2 appendix V D), and use octadecylsilane chemically bonded silica as filler, and calculate the dissolution of each tablet.

| Samples | Dissolution (%) | | |
|---|---|---|---|
| | 15 min | 30 min | 45 min |
| Contrastive 7 | 50.2 | 75.1 | 96.5 |
| 18 | 73.0 | 95.2 | 99.7 |
| 19 | 60.8 | 87.6 | 97.4 |
| 20 | 89.3 | 95.0 | 98.9 |

(5) Comparison on Dissolution of Dipyridamole Tablets of Contrastive Example 8 and Example 21

Method of Dissolution Experiment: following dissolution mensuration (Chinese Pharmacopoeia 2005 Volume 2 appendix X C No. 1), take samples and make 900 ml pH 4.0 acetate buffer solution (0.05 mol/L acetic acid –0.05 mol/L sodium acetate=16.4:3.6) as solvent, rotation rate is 50 rpm, carry on according to the mensuration. According to ultraviolet-visible spectrophotometry (Chinese Pharmacopoeia 2005 Volume 2 appendix IV A), detect absorbance at 283 nm respectively, and calculate the dissolution of each tablet.

| | Dissolution (%) | | |
|---|---|---|---|
| Example | 5 min | 15 min | 30 min |
| Contrastive 8 | 75.3 | 87.1 | 89.7 |
| 21 | 85.9 | 95.4 | 97.0 |

(6) Comparison on Dissolution of Iloperidone Tablets in Contrastive Example 10 and Examples 86, 87

Method of Dissolution Experiment: following dissolution mensuration (Chinese Pharmacopoeia 2005 Volume 2 appendix X C No. 2), take samples and make 500 ml 0.1 mol/L hydrochloric acid solution as dissolution medium, rotation rate is 50 rpm, carry on according to the mensuration, take 5 ml solution at the $10^{th}$, $20^{th}$, $30^{th}$, $45^{th}$ min respectively, replenish each 5 ml dissolution medium, filter the samples and discard the filtrate of prefiltration, take subsequent filtrate as sample solution, and prepare reference solution. According to ultraviolet-visible spectrophotometry (Chinese Pharmacopoeia 2005 Volume 2 appendix IV A), detect absorbance at 228 nm and calculate the dissolution of each tablet.

| | Dissolution (%) | | | |
|---|---|---|---|---|
| Example | 10 min | 20 min | 30 min | 45 min |
| Contrastive 10 | 32.6 | 50.8 | 64.2 | 75.1 |
| 86 | 78.2 | 96.2 | 98.6 | 102.3 |
| 87 | 76.9 | 93.1 | 97.7 | 101.5 |

EFFECT EXAMPLE 3

Accelerated Stability Experiment

Add experiment samples into high density polyethylene plastic bottle respectively, sealed and add them in accelerated inspection box, after the accelerated test for 3 months at temperature 40° C.±2° C. and relative humidity 75%±5%, carry on the detection of stability on related items.

(1) Comparison on Stability of Aripiprazole Tablets of Contrastive Example 3 and Examples 3~4

Detection Method of Content and the Related Substances: take appropriate dosage of samples, shake and dissolve it by mobile phase ultrasonic and make the solution containing appropriate aripiprazole per ml as the tested solution, and prepare reference solution. Detection is respectively followed by high performance liquid chromatography (Chinese Pharmacopoeia 2005 Volume 2 appendix V D), and use octadecylsilane chemically bonded silica as filler. The determination of content is according to the external standard method, the content of the related substance is calculated by main component self-calibrated method. The determination method of dissolution is the same as that in Effect Example 2 (1).

| | Character | | Content (%) | | Dissolution at the $45^{th}$ min (%) | | Related Substance (%) | |
|---|---|---|---|---|---|---|---|---|
| Example | Prior to acceleration | After acceleration | Prior to acceleration | After acceleration | Prior to acceleration | After acceleration | Prior to acceleration | After acceleration |
| Contrastive 3 | White tablet | White tablet | 99.2 | 99.6 | 97.3 | 94.4 | 0.16 | 0.20 |
| 3 | White tablet | White tablet | 98.9 | 98.8 | 98.5 | 97.7 | 0.18 | 0.30 |
| 4 | White tablet | White tablet | 100.1 | 100.3 | 99.7 | 99.5 | 0.17 | 0.23 |

(2) Comparison on Stability of Eszopiclone Preparations of Contrastive Example 5, Examples 6~9 and 11

Determination Method for Content: take appropriate dosage of samples (equal to eszopiclone 3 mg), add it into 250 ml measuring flask, add appropriate dosage of 0.02 mol/L hydrochloric acid, shake up and filter, take subsequent filtrate as test solution; separately, take appropriate dosage of eszopiclone as reference substance, make the solution containing 12 μg eszopiclone per 1 ml with 0.02 mol/L hydrochloric acid as reference solution. According to ultraviolet-visible spectrophotometry (Chinese Pharmacopoeia 2005 Volume 2 appendix IV A), detect absorbance at 304 nm respectively and calculate the content.

Determination Method for the Related Substance: Determination is followed by high performance liquid chromatography (Chinese Pharmacopoeia 2005 Volume 2 appendix V D), and use octadecylsilane chemically bonded silica as filler; and use acetonitrile –0.05 mol/L ammonium sulfate solution (40:60) as mobile phase; detection wavelength is 304 nm, and the chromatogram of test solution and reference solution are calculated by main component self-calibrated method.

Test Method for Dissolution which is the same as that in the Effect Example 2 (2).

| Example | Character | | Content (%) | | Dissolution at the 30th min (%) | | Related Substance (%) | |
|---|---|---|---|---|---|---|---|---|
| | Prior to acceleration | After acceleration | Prior to acceleration | After acceleration | Prior to acceleration | After acceleration | Prior to acceleration | After acceleration |
| Contrastive 5 | White tablet | White tablet | 98.6 | 98.4 | 88.9 | 83.2 | 0.09 | 0.58 |
| 6 | White tablet | White tablet | 99.2 | 99.0 | 95.2 | 94.8 | 0.10 | 0.50 |
| 7 | Content is white granules | Content is white granules | 100.3 | 100.1 | 99.8 | 99.5 | 0.09 | 0.49 |
| 8 | White tablet | White tablet | 98.4 | 98.7 | 98.3 | 99.1 | 0.10 | 0.46 |
| 9 | White tablet | White tablet | 99.7 | 99.4 | 99.2 | 99.4 | 0.09 | 0.43 |
| 11 | White tablet | White tablet | 97.5 | 97.8 | 98.4 | 97.2 | 0.08 | 0.42 |

(3) Comparison on Stability of Zopiclone Tablets of Contrastive Example 6, Examples 12, 13 and 15

Determination Method for Content: take appropriate dosage of samples (equal to zopiclone 3 mg), add it into 250 ml measuring flask, add appropriate dosage of 0.02 mol/L hydrochloric acid, shake up and filter, take subsequent filtrate as test solution; separately take appropriate dosage of zopiclone as reference substance, make the solution containing 12 µg eszopiclone per 1 ml with 0.02 mol/L hydrochloric acid as reference solution. According to ultraviolet-visible spectrophotometry (Chinese Pharmacopoeia 2005 Volume 2 appendix IV A), detect absorbance at 304 nm respectively and calculate the content.

Determination Method for the Related Substance: Determination is followed by high performance liquid chromatography (Chinese Pharmacopoeia 2005 Volume 2 appendixV D), and use octadecylsilane chemically bonded silica as filler, detection wavelength is 304 nm. The chromatograms of test solution and reference solution are calculated by main component self-calibrated method.

Test Method for Dissolution is the same as that in the Effect Example 2 (3).

| Example | Character | | Content (%) | | Dissolution at the 30th min (%) | | Related Substance (%) | |
|---|---|---|---|---|---|---|---|---|
| | Prior to acceleration | After acceleration | Prior to acceleration | After acceleration | Prior to acceleration | After acceleration | Prior to acceleration | After acceleration |
| Contrastive 6 | White tablet | White tablet | 99.1 | 98.8 | 89.3 | 87.1 | 0.09 | 0.60 |
| 12 | White tablet | White tablet | 99.7 | 99.3 | 98.5 | 99.1 | 0.11 | 0.51 |
| 13 | White tablet | White tablet | 101.4 | 100.7 | 100.2 | 99.8 | 0.10 | 0.48 |
| 15 | White tablet | White tablet | 99.1 | 99.5 | 99.8 | 99.1 | 0.09 | 0.50 |

(4) Comparison on Stability of Risperidone Tablets of Contrastive Example 7 and Example 18

Determination Method for Content and the Related Substance: take appropriate dosage of samples, shake and dissolve it by mobile phase ultrasonic and make the solution containing appropriate risperidone per ml as the test solution, and prepare reference solution. Determination is respectively followed by high performance liquid chromatography (Chinese Pharmacopoeia 2005 Volume 2 appendix V D), and use octadecylsilane chemically bonded silica as filler. The determination of content is according to the external standard method, the content of the related substance is calculated by main component self-calibrated method.

The determination method of dissolution is the same as that in the Effect Example 2 (4).

| Example | Character | | Content (%) | | Dissolution at the 45$^{th}$ min (%) | | Related Substance (%) | |
|---|---|---|---|---|---|---|---|---|
| | Prior to acceleration | After acceleration | Prior to acceleration | After acceleration | Prior to acceleration | After acceleration | Prior to acceleration | After acceleration |
| Contrastive 7 | White tablet | White tablet | 99.2 | 98.0 | 96.5 | 95.0 | 0.12 | 0.23 |
| 18 | White tablet | White tablet | 101.2 | 100.6 | 99.7 | 98.0 | 0.12 | 0.26 |

(5) Comparison on Stability of Dipyridamole Tablets of Contrastive Example 8 and Example 21

Determination Method for Content: take appropriate dosage of samples (equal to 50 mg dipyridamole), add it into 100 ml measuring flask, add appropriate dosage of 0.01 mol/L hydrochloric acid, shake and dissolve it and dilute to scale with 0.01 mol/L hydrochloric acid, shake up and filter, make the solution containing 10 μg dipyridamole per 1 ml with 0.01 mol/L hydrochloric acid as test solution. According to ultraviolet-visible spectrophotometry (Chinese Pharmacopoeia 2005 Volume 2 appendix IV A), detect absorbance at 283 nm.

Determination Method for the Related Substance: take appropriate dosage of samples, make the solution containing 1.0 mg dipyridamole with methyl alcohol as test solution, and prepare the solution containing 10 μg dipyridamole per ml as reference solution. Determination is respectively followed by high performance liquid chromatography (Chinese Pharmacopoeia 2005 Volume 2 appendix V D), and use octadecylsilane chemically bonded silica as filler, detection wavelength is 288 nm, and calculate by main component self-calibrated method.

The determination method for dissolution is the same as that in the Effect Example 2 (5).

EFFECT EXAMPLE 4

Content Uniformity Experiment

Determine content of each tablet (the determination method for content is the same as that in Effect Example 3 (2)), and calculate the content uniformity (A+1.80 S) according to Chinese Pharmacopoeia 2005 appendix XE content uniformity test.

| | Result | | |
|---|---|---|---|
| Example | Average Content (%) | Standard Deviation(S) | Content Uniformity (A + 1.80S) |
| Contrastive 3 | 99.2 | 2.4 | 5.1 |
| 3 | 98.9 | 1.3 | 3.4 |
| Contrastive 5 | 101.07 | 2.16 | 4.96 |
| 6 | 101.88 | 1.54 | 4.65 |
| 36 | 100.09 | 1.75 | 3.23 |
| Contrastive 6 | 98.15 | 2.31 | 6.00 |
| 12 | 101.06 | 2.06 | 4.77 |
| Contrastive 7 | 99.2 | 5.3 | 10.3 |
| 18 | 101.2 | 3.0 | 6.6 |

The invention claimed is:

1. A production method of a solid preparation, comprising:
   dissolving a water-insoluble alkaline active pharmaceutical ingredient in an acidifier-containing acid solution to obtain a medicated acid liquid; then
   homogeneously mixing an alkalizer, adjuvants and the medicated acid liquid, and carrying out wet granulation, wherein the water-insoluble alkaline active pharmaceutical ingredient is eszopiclone, diazepam, estazolam,

| Example | Character | | Content (%) | | Dissolution at the 30$^{th}$ min (%) | | Related Substance (%) | |
|---|---|---|---|---|---|---|---|---|
| | Prior to acceleration | After acceleration | Prior to acceleration | After acceleration | Prior to acceleration | After acceleration | Prior to acceleration | After acceleration |
| Contrastive 8 | Yellow tablet | Yellow tablet | 98.5 | 98.4 | 89.7 | 86.5 | 0.10 | 0.42 |
| 21 | Yellow tablet | Yellow tablet | 98.3 | 98.0 | 97.0 | 95.5 | 0.08 | 0.40 | alprazolam, zopiclone, aripiprazole, risperidone, mifepristone, perphenazine, digoxinum, agomelatine, iloperidone, paliperidone, olanzapine, haloperidol, dipyridamole, carbimazole, metoclopramide, minoxidil or reserpine, and the alkalizer is a reagent that reduces the acidity of the medicated acid liquid.

2. The method according to claim 1, wherein a content of the water-insoluble alkaline active pharmaceutical ingredient in the solid preparation is below 20% by weight.

3. The method according to claim 1, wherein the acidifier is selected from the group consisting of an inorganic acid and an organic acid.

4. The method according to claim 1, wherein an amount of the acidifier is 1~1.5 times greater than a minimum amount which can completely dissolve the water-insoluble alkaline active pharmaceutical ingredient.

5. The method according to claim 1, wherein a molar ratio of the acidifier to the water-insoluble alkaline active pharmaceutical ingredient is 0.1~2.5.

6. The method according to claim 1, wherein
a solvent of the acidifier-containing acid solution is water, an organic solvent, or a mixture of water and an organic solvent, and ions of the acidifier can be dissociated in the solvent; and
the organic solvent is better than water to solubilize the water-insoluble alkaline active pharmaceutical ingredient.

7. The method according to claim 1, wherein an amount of the solvent of the acid solution is 5~100% by mass relative to a mass of dry materials in the wet granulation.

8. The method according to claim 1, wherein the method further comprises:
at the same time or after the dissolving of the water-insoluble alkaline active pharmaceutical ingredient in the acidifier-containing acid solution, adding one or more adjuvants selected from the group consisting of surfactants, solubilizers, and water-soluble carriers of solid dispersion, wherein
the resultant medicated acid liquid is used for the homogeneous mixing of the alkalizer and the adjuvants with the medicated acid liquid to carry out wet granulation; and
when the water-soluble carriers of solid dispersion and the water-insoluble alkaline active pharmaceutical ingredient are added into the acidifier-containing acid liquid at the same time, an amount of the water-soluble carriers of solid dispersion is controlled to ensure complete dissolution of the water-insoluble alkaline active pharmaceutical ingredient in the acidifier-containing acid liquid.

9. The method according to claim 8, wherein
at the same time or after the dissolving of the water-insoluble alkaline active pharmaceutical ingredient in the acidifier-containing acid solution, one or more surfactant and/or solubilizer and one or more water-soluble carriers of solid dispersion are added;
an amount of the surfactants and/or solubilizers is 0.05~5 times a mass of the water-insoluble alkaline active pharmaceutical ingredient; and
the amount of the water-soluble carriers of solid dispersion is 1~10 times the mass of the water-insoluble alkaline active pharmaceutical ingredient.

10. The method according to claim 1, wherein in the preparation of the medicated acid liquid,
when a solvent of the acidifier-containing acid solution is water, a preparation temperature is 40~80° C.;
when the solvent is a mixture of water and an organic solvent, the preparation temperature is 40~70° C.; and
when the solvent is ethanol, the preparation temperature is 30~50° C.

11. The method according to claim 1, wherein the alkalizer is an inorganic alkali, a salt of alkali and an acid, a conjugate base of an organic acid, or an acid having an acidity lower than that of a second acidic acidifier and capable of forming a buffer pair with the second acidic acidifier.

12. The method according to claim 1, wherein a pairing of the acidifier and the alkalizer is selected from the group consisting of:
Type 1: the acidifier is an inorganic acid, and the alkalizer is an inorganic alkali;
Type 2: the acidifier is an inorganic acid, and the alkalizer is a salt of an inorganic acid and an alkali;
Type 3: the acidifier is an inorganic acid, and the alkalizer is a salt of an organic acid and an alkali;
Type 4: the acidifier is an organic acid, and the alkalizer is a conjugate base of an organic acid;
Type 5: the acidifier is an organic acid, and the alkalizer is an inorganic alkali or a salt of an inorganic acid and an alkali; and
Type 6: the acidifier is an inorganic acid, and the alkalizer is an acid capable of forming a buffer pair with an inorganic acid.

13. The method according to claim 12, wherein an amount of the acidifier and the alkalizer meet the following relations:
a value of Formula 1 is 0.01~1.5;

(mole of the alkalizer*A)/(mole of the acidifier*B)   Formula 1 wherein,
when the pairing of the acidifier and the alkalizer is the Type 1, 2 or 5 pairing, A equals a total anionic valency of the alkalizer molecule minus a number of hydrogen ions in the alkalizer molecule;
when the pairing of the acidifier and the alkalizer is the Type 1, 2, 3 or 6 pairing, B equals a number of hydrogen ions in the acidifier molecule;
when the pairing of the acidifier and the alkalizer is the Type 4 pairing, A/B equals 1;
when the pairing of the acidifier and the alkalizer is the Type 5 pairing, B equals 1;
when the pairing of the acidifier and the alkalizer is the Type 3 or 6 pairing, A equals 1; and
when the water-insoluble alkaline active pharmaceutical ingredient is iloperidone, the acidifier is acetic acid, the alkalizer is sodium hydroxide, and the value of Formula 1 equals 0.99~1.01.

14. The method according to claim 1, wherein a mode of the homogeneously mixing of the alkalizer, the adjuvants and the medicated acid liquid, and carrying out wet granulation is selected from the group consisting of:
method (i): homogeneously mixing the alkalizer or a solution containing the alkalizer with the adjuvants to form a mixture, and then homogeneously mixing the mixture with the medicated acid liquid, and carrying out extrusion granulation or stirring granulation;
method (ii): homogeneously mixing the medicated acid liquid with the alkalizer or a solution containing the alkalizer to obtain a granulating solution, and then carrying out extrusion granulation, stirring granulation, fluidized spray granulation or centrifugal spray granulation with the granulating solution and the adjuvants;
method (iii): homogeneously mixing the medicated acid liquid with the adjuvants to form a mixture, and then homogeneously mixing the mixture with a solution containing the alkalizer, and carrying out extrusion granulation or stirring granulation; and method (iv): homogeneously mixing the medicated acid liquid, the adjuvants whose amount is below one-third, and the alkalizer or a solution containing the alkalizer to form a mixture, and then mixing the mixture with the remaining adjuvants and carrying out extrusion granulation or stirring granulation.

15. The method according to claim 1, further comprising forming the solid preparation into tablets or capsules.

16. A solid preparation produced by the method according to claim 1.

17. The method according to claim 3, wherein the acidifier is selected from the group consisting of hydrochloric acid, citric acid, tartaric acid, malic acid, fumaric acid, succinic acid, maleic acid, lactic acid, acetic acid, hydrobromic acid, sulfuric acid, nitric acid and phosphoric acid.

18. The method according to claim 1, wherein the water-insoluble alkaline active pharmaceutical ingredient is iloperidone, and the acidifier is acetic acid or citric acid.

19. The method according to claim 6, wherein the organic solvent is a water-soluble organic solvent selected from the group consisting of ethanol, propylene glycol, glycerin, acetone, isopropyl alcohol and tertiary butyl alcohol.

20. The method according to claim 1, wherein the alkalizer is selected from the group consisting of sodium hydroxide, sodium carbonate, disodium hydrogen phosphate, sodium citrate, sodium tartrate, sodium malate, sodium acetate, glycine and alanine.

21. The method according to claim 1, wherein a pairing of the acidifier and the alkalizer is selected from the group consisting of hydrochloric acid and sodium hydroxide, hydrochloric acid and sodium carbonate, hydrochloric acid and disodium hydrogen phosphate, hydrochloric acid and sodium citrate, hydrochloric acid and sodium tartrate, hydrochloric acid and sodium malate, hydrochloric acid and sodium acetate, citric acid and sodium citrate, tartaric acid and sodium tartrate, malic acid and sodium malate, acetic acid and sodium acetate, acetic acid and sodium hydroxide, citric acid and sodium hydroxide, citric acid and sodium carbonate, malic acid and sodium carbonate, malic acid and disodium hydrogen phosphate, citric acid and disodium hydrogen phosphate, hydrochloric acid and glycine, hydrochloric acid and alanine, phosphoric acid and sodium hydroxide, phosphoric acid and sodium carbonate, and phosphoric acid and disodium hydrogen phosphate.

* * * * *